US011525143B2

(12) United States Patent
Hemerly et al.

(10) Patent No.: US 11,525,143 B2
(45) Date of Patent: Dec. 13, 2022

(54) METHOD FOR PROMOTING AN INCREASE IN PLANT BIOMASS, PRODUCTIVITY, AND DROUGHT RESISTANCE

(71) Applicant: Universidade Federal Do Rio De Janeiro, Rio de Janeiro (BR)

(72) Inventors: Adriana Silva Hemerly, Rio de Janeiro (BR); Paulo Cavalcanti Gomes Ferreira, Rio de Janeiro (BR); Pan Gong, Ghent (BE); Hilde Nelissen, Ghent (BE); Dirk Inzé, Moorsel-Aalst (BE); Maria Fatima Grossi De Sá, Brasília (BR); Marcos Fernando Basso, Brasília (BR); Carolina Vianna Morgante, Brasília (BR); Maria Eugenia Lisei-De-Sa, Brasília (BR)

(73) Assignee: Universidade Federal Do Rio De Janeiro, Rio de Janeiro (BR)

(*) Notice: Subject to any disclaimer, the term of this patent is extended or adjusted under 35 U.S.C. 154(b) by 11 days.

(21) Appl. No.: 16/866,467

(22) Filed: May 4, 2020

(65) Prior Publication Data
US 2020/0347399 A1 Nov. 5, 2020

Related U.S. Application Data

(63) Continuation-in-part of application No. 15/064,435, filed on Mar. 8, 2016, now Pat. No. 10,647,988, which is a continuation-in-part of application No. PCT/BR2015/000024, filed on Mar. 2, 2015.

(30) Foreign Application Priority Data

Feb. 28, 2014 (BR) .......................... 1020140048812

(51) Int. Cl.
*C12N 15/82* (2006.01)
(52) U.S. Cl.
CPC .... *C12N 15/8273* (2013.01); *C12N 2310/141* (2013.01)
(58) Field of Classification Search
None
See application file for complete search history.

(56) References Cited

U.S. PATENT DOCUMENTS

| | | | |
|---|---|---|---|
| 5,034,323 A | 7/1991 | Jorgensen et al. | |
| 5,107,065 A | 4/1992 | Shewmaker et al. | |
| 5,283,184 A | 2/1994 | Jorgensen et al. | |
| 5,453,566 A | 9/1995 | Shewmaker et al. | |
| 5,759,829 A | 6/1998 | Shewmaker et al. | |
| 5,942,657 A | 8/1999 | Bird et al. | |
| 2003/0175965 A1 | 9/2003 | Lowe et al. | |
| 2003/0180945 A1 | 9/2003 | Wang et al. | |
| 2004/0031072 A1* | 2/2004 | La Rosa ................ | C07H 21/04 800/278 |
| 2008/0213871 A1 | 9/2008 | Sticklen | |
| 2009/0265815 A1 | 10/2009 | Alexandrov et al. | |
| 2010/0170007 A1 | 7/2010 | Bielenberg et al. | |
| 2012/0198585 A1 | 8/2012 | Xiao et al. | |
| 2014/0283215 A1 | 9/2014 | Steffens | |
| 2017/0037426 A1 | 2/2017 | Alexandrov et al. | |

FOREIGN PATENT DOCUMENTS

| | | |
|---|---|---|
| EP | 2295582 A2 | 3/2011 |
| EP | 2391642 A2 | 12/2011 |
| WO | 2004/029257 A1 | 4/2004 |
| WO | 2006/105106 A2 | 10/2006 |
| WO | 2011/130815 A2 | 10/2011 |
| WO | 2015127521 * | 3/2015 |
| WO | 2015/127521 A1 | 9/2015 |

OTHER PUBLICATIONS

Alonso, et al. (Science 301.5633 (2003): 653-657) . (Year: 2003).*
Ali et al., RNA interference in designing transgenic crops, (2010) GM Crops 1:4, 207-213.
Alonso et al. (Science, 301:653-657, 2003).
Arziman et al. (Nucleic Acids Research, 33:582-588, 2005).
Belide et al., Modification of seed oil composition in *Arabidopsis* by ailincial microRNA-mediated gene silencing, (2012) Frontiers in Plant Science 3, 168, 6 pages.
Bhaskar et al., Suppression of the Vacuolar Invertase Gene Prevents Cold-Induced Sweetening in Potato, (2010) Plant Physiology 154: 939-948.
Bruening (Proc. Natl. Acad. Sci., 95:13349-13351, 1998).
Colliver et al. (Plant molecular Biology, 35:509-522, 1997).
Elomaa et al. (Molecular Breeding, 2:41-50, 1996).
Emery et al. (Current Biology 13:1768-1774, 2003).
Gutterson (HortScience 30:964-966, 1995).
International Search Report for International Application No. PCT/BR2015/000024, dated Jul. 9, 2015, 5 pages.
International Written Opinion for International Application No. PCT/BR2015/000024, dated Jul. 9, 2015, 6 pages.
Jorgensen et al., Chalcone synthase cosuppression phenotypes in petunia flowers: comparison of sense vs. antisense constructs and single-copy vs. complex T-DNA sequences (1996) Plant Mol. Biol. 31:957-973.
Joseph Ecker (Germplasm / Stock: SALK->_022332 Submitted and available on public domain on Aug. 9, 2002).
Kasai and Kanazawa, RNA silencing as a tool to uncover gene function and engineer novel traits in soybean, (2012) Breeding Science 61: 468-479.

(Continued)

*Primary Examiner* — Charles Logsdon
(74) *Attorney, Agent, or Firm* — TraskBritt

(57) ABSTRACT

Described are methods for promoting increase in plant biomass and yield. This increase has its visible effects in organs such as leaf, stem, root and production of fruits and seeds. Further described is the increase in tolerance of those plants to drought, generating plants better adapted to the environmental changes, improving their growth, biomass and yield.

20 Claims, 12 Drawing Sheets
(4 of 12 Drawing Sheet(s) Filed in Color)
Specification includes a Sequence Listing.

(56) References Cited

OTHER PUBLICATIONS

Liu et al., High-Stearic and High-Oleic Cottonseed Oils Produced by Hairpin RNA-Mediated Post-Transcriptional Gene Silencing, (2002) Plant Physiol. 129:1732-1743.
Mansoor et al., Engineering novel traits in plants through RNA interference, (2006) Trends in Plant Science 11: 559-565.
Masuda, H.P. et al.: "ABAP1 is a novel plant Armadillo BTB protein involved in DNA replication and transcription." EMBO J. 27:2746-2756, 2008.
PCT International Search Report, PCT/BR2015/000024, dated Jul. 9, 2015.
PCT International Written Opinion, PCT/BR2015/000024, dated Jul. 9, 2015.
Ralph et al., NMR characterization of altered lignins extracted from tobacco plants down-regulated for lignification enzymes cinnamyl-alcohol dehydrogenase and cinnamoyl-CoA reductase, (1998) Proc. Natl. Acad. Sci. USA 95: 12803-12808.
Shimada et al., Increase of amylose content of sweetpotato starch by RNA interference of the starch branching enzyme II gene (IbSBEII), (2006) Plant Biotechnology 23, 85-90.
Toppino et al., Reversible male sterility in eggplant (*Solanum melongena* L.) by artificial micro-RNA-mediated silencing of general transcription factor genes, (2011) Plant Biotechnology Journal 9: 684 692.
Verma and Dwivedi, Lignin genetic engineering for improvement of wood quality: Applications in paper and textile industries, fodder and bioenergy production, (2014) South African Journal of Botany 9: 107-125.
Waterhouse and Helliwell, Exploring Plant Genomes by RNA-Induced Gene Silencing, (2003) Nat. Rev. Genet. 4:29-38.
Younis et al., RNA Interference (RNAi) Induced Gene Silencing: A Promising Approach of Hi Tech Plant Breeding, (2014) Int. J. Biol. Sci. 10: 1150-1158.
Zhou et al. (Plant Physiol., June 162(2): 1030-1040; Published Jun. 2013; first published on line May 8, 2013).
Zhou, X.F. et al.: "CYCLIN H;1 regulates drought stress responses and blue light-induced stomatal opening by inhibiting reactive oxygen species accumulation in *Arabidopsis*." Plant Physiology, 162:1030-1041, 2013.
Zuker et al., Modification of flower color and fragrance by antisense suppression of the flavanone 3-hydroxylase gene, (2002) Molecular Breeding 9: 33-41.
Aladjem "Replication in context: dynamic regulation of DNA replication patterns in metazoans" Nature Reviews Genetics, v. 8, n. 8, pp. 588 600, (Jul. 2007).
Berckmans et al. "Transcriptional control of the cell cycle" Current opinion in plant biology, v. 12, n. 5, pp. 599-605(Aug. 2009).
Blow et al. "Preventing re replication of chromosomal DNA" Nat. Rev. Mol. Cell. Biol., v.6, n.6, pp. 476-486 (Jun. 2005).
De Veylder et al. "The ins and outs of the plant cell cycle" Nature Reviews Molecular Cell Biology, v. 8, n. 8, pp. 655 665, 2007.
Machida et al. "Right Place, Right Time, and Only Once: Replication Initiation in Metazoans" Cell, vol. 123, 13-24, Oct. 7, 2005.
Masuda et al. "ABAP1 is a novel plant Armadillo BTB protein involved in DNA replication and transcription" The EMBO journal, v. 27, n. 20, pp. 2746-2756, 22 out. (Sep. 2008).
Morison et al. "Improving water use in crop production" Philosophical transactions of the Royal Society of London. Series B, Biological sciences, vol. 363, No. 1491, pp. 639-658, 12 (Feb. 2008).
Parry et al. "An integrated approach to crop genetic improvement" Journal of integrative plant biology, vol. 54, No. 4, pp. 250-259 (Apr. 2012).
Ramirez-Parra et al. "Balance between cell division and differentiation during plant development" The International Journal of Developmental Biology, v. 49, (Feb. 2005).
Sun et al. "DNA replication origins, ORC/DNA interaction, and assembly of pre replication complex in eukaryotes" Acta. Biochim. Biophys. Sin., vol. 42, No. 7, pp. 433-439, (Jul. 2010).

* cited by examiner

P value: 0.05

*FIG. 9A* A) dsRNA strategy in soybean
*FIG. 9B* B) amiRNA artificial strategy in soybean
*FIG. 9C* C)
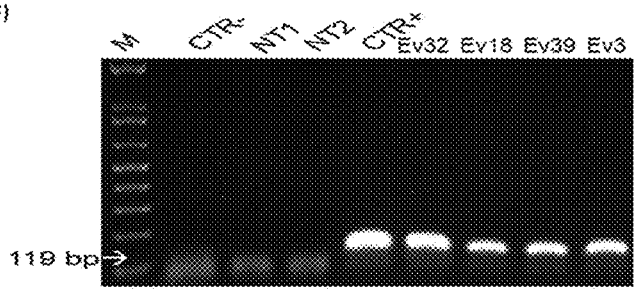
*FIG. 9D*
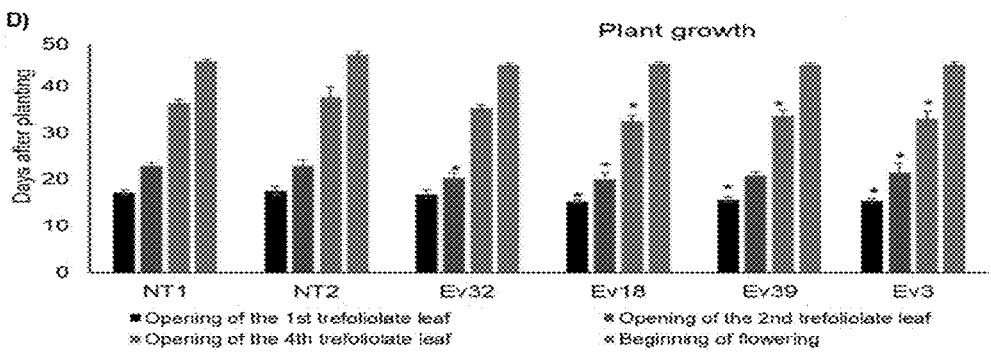
*FIG. 9E*
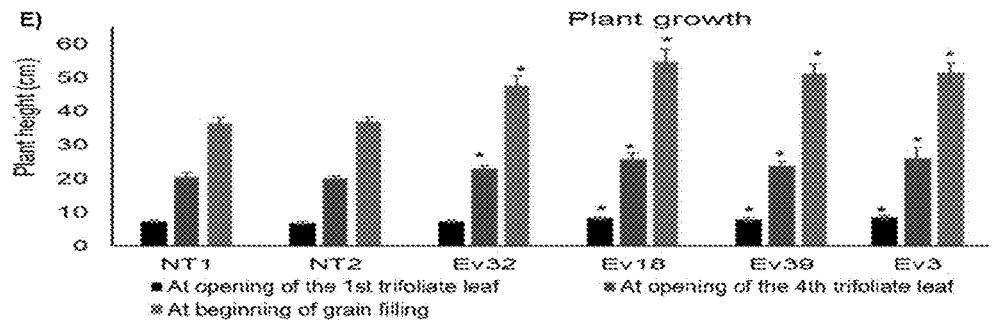
*FIG. 9F*
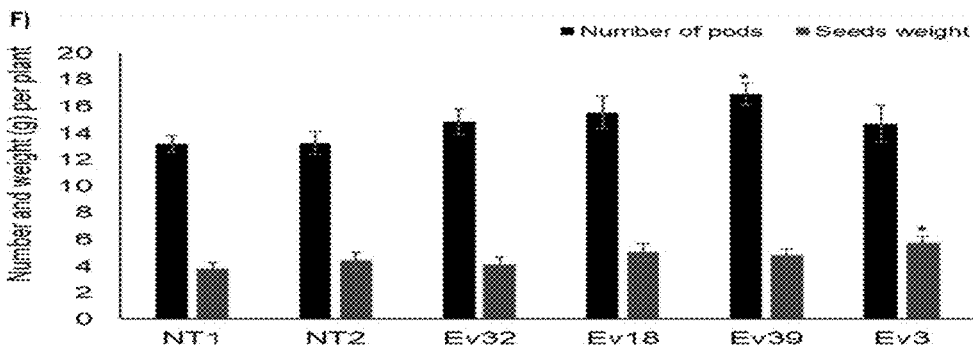

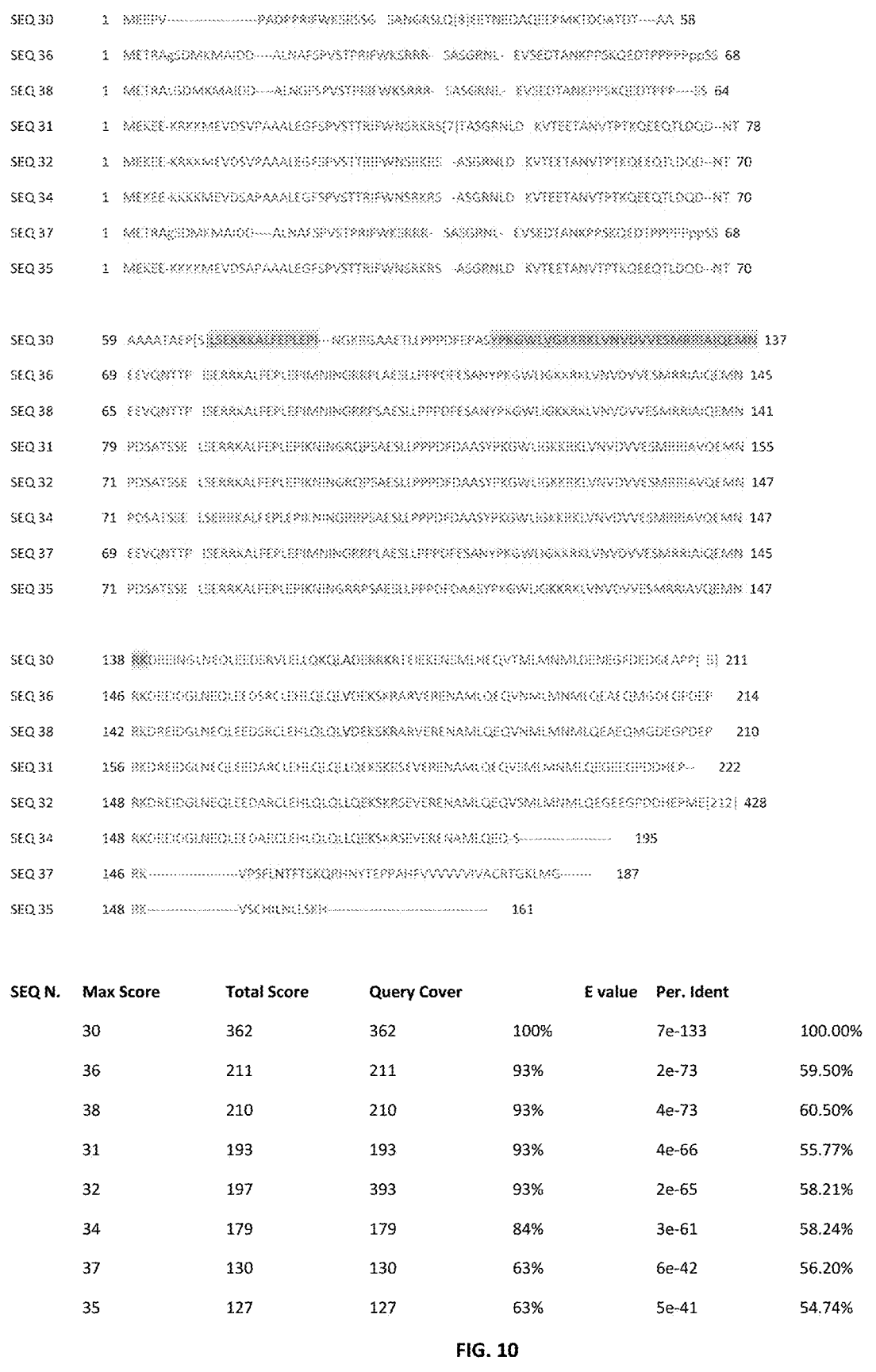

| SEQ N. | Max Score | Total Score | Query Cover | E value | Per. Ident | |
|---|---|---|---|---|---|---|
| | 30 | 362 | 362 | 100% | 7e-133 | 100.00% |
| | 36 | 211 | 211 | 93% | 2e-73 | 59.50% |
| | 38 | 210 | 210 | 93% | 4e-73 | 60.50% |
| | 31 | 193 | 193 | 93% | 4e-66 | 55.77% |
| | 32 | 197 | 393 | 93% | 2e-65 | 58.21% |
| | 34 | 179 | 179 | 84% | 3e-61 | 58.24% |
| | 37 | 130 | 130 | 63% | 6e-42 | 56.20% |
| | 35 | 127 | 127 | 63% | 5e-41 | 54.74% |

FIG. 10

METHOD FOR PROMOTING AN INCREASE IN PLANT BIOMASS, PRODUCTIVITY, AND DROUGHT RESISTANCE

CROSS-REFERENCE TO RELATED APPLICATIONS

This application is a continuation-in-part of co-pending U.S. patent application Ser. No. 15/064,435, filed Mar. 8, 2016 (U.S. Pat. No. 10,647,988, May 12, 2020), which is a continuation-in-part of pending International Patent Application PCT/BR2015/000024, filed Mar. 2, 2015, designating the United States of America and published as International Patent Publication WO 2015/127521 A1 on Sep. 3, 2015, which claims the benefit under Article 8 of the Patent Cooperation Treaty to Brazilian Patent Application Serial No. BR1020140048812, filed Feb. 28, 2014, the disclosure of each of which is hereby incorporated herein in its entirety by this reference.

TECHNICAL FIELD

This application relates to biotechnology generally, and particularly to a method for promoting an increase in plant growth as a whole, leading, e.g., to an increase of biomass and seed yield and associated plants, progeny and, e.g., seeds. This increase has its visible effects in plant organs such as leaf, stem, roots, and in fruit production. Furthermore, the method is capable of increasing tolerance of the treated plants to drought.

BACKGROUND

The increasing world population has led to a rising demand for food, energy, and natural resources. Food production is closely related to water availability. Water, once available in much of the earth's surface, is the limiting factor in agricultural productivity. Thus, the steady increase of agriculture, together with climate change, is making the use of water resources unsustainable. In this scenario, a need exists to increase agricultural productivity in a sustainable manner, that is, to produce more using less water (Morison et al., 2008; FAO, 2012). Another problem to be faced is the availability of areas for cultivation because, increasingly, these areas are scarce, and a great concern exists for the conservation and preservation of biodiversity.

Many efforts are being made to reduce the amount of water used for agriculture, and to produce "more by drop" and per hectare. One way to achieve that increased agricultural productivity can be through plant breeding. In such a way, it is possible to increase yield, but also minimize losses by biotic and abiotic stresses (Morison et al., 2008; Parry and Hawkesford, 2012).

However, to improve plant growth, intervention in the cell cycle of the plant is often needed. As it is well known, the cell cycle is a conserved and critical step in the life cycle of eukaryotic organisms where the genetic material from the mother cell is duplicated and divided between two daughter cells. This process is coordinated with changes in the architecture of the cell and has four well-defined stages: the stage of synthesis, mitosis and two intervals, known as gap1 (G1) and gap2 (G2).

In the synthesis phase (S phase), the DNA is replicated to produce copies of the two daughter cells. During the G2 gap, new proteins are synthesized and the cell doubles in size. Later, in mitosis (M phase), the replicated chromosomes are separated so that each daughter cell receives a copy.

In the interval between mitosis and DNA synthesis phase (G1 gap), nuclear DNA is prepared for replication.

Errors in this cycle progression could have serious consequences for the integrity of the genome and, therefore, for the development of the organism. Thus, to ensure that the events occur properly, and the DNA is duplicated only once, the cells have checkpoints between transitions (Ramires-Parra et al., 2005; Berkmans and de Veylder, 2009; de Veylder et al., 2007).

The first checkpoint determines whether the cell enters the DNA synthesis phase (G1) or remains in the quiescent state. The first step of the DNA synthesis phase is the formation of a structure that will regulate the entire process of cell division, the pre-replicative complex (pre-RC) (Machida et al., 2005; M. I. Aladjem, 2007).

The first step in the formation of the pre-RC is the recognition of DNA replication origins by the Origin Recognition Complex (ORC). After this recognition, the CDC6 and CDT1 proteins join the ORC complex and will recruit the MCM complex, which has helicase activity, culminating in the licensing of DNA for replication (Machida et al., 2005; Blow and Dutta, 2005; Sun and Kong, 2010).

It was revealed in an article by one group (H. P. Masuda, L. M. Cabral, L. De Veylder, M. Tanurdzic, J. De Almeira Engler, D. Geelen, D. Inze, R. A. Martienssen, P. A. Ferreira, and A. S. Hemerly—ABAP1 is a novel plant protein armadillo BTB involved in DNA replication and transcription, EMBO Journal, 2008), that *Arabidopsis thaliana* has a new cell cycle regulation mechanism in which the ABAP1 protein plays a central role. This protein interacts with members of the DNA replication machinery, transcription factors and other classes of proteins (Masuda et al., 2008). One of these proteins with which ABAP1 interacts was called AIP10. Knockout plants for AIP10 gene have larger roots and leaves, produce more seeds and have greater resistance to water stress situations.

Other research and disclosures have also been made to promote increased plant biomass, however, by different methods. For example, International Application Publication WO 2011/130815, the contents of which are incorporated herein by this reference, discloses a method for increasing plant biomass by introducing a polynucleotide sequence into the plant genome.

Through the use of recombinant DNA, in the patent application EP2295582, the contents of which are incorporated herein by this reference, the inventor seeks the enhancement of plant specimens by controlling nucleic acid expression of CDC27A. The disclosure described in the application WO 2004/029257, the contents of which are incorporated herein by this reference, seeks to alter the development of a plant.

The patent application EP2391642, the contents of which are incorporated herein by this reference, refers to a protein complex that promotes plant growth. More specifically, the disclosure relates to the use of specific proteins of the anaphase-promoting complex/cyclosome to increase plant growth rates and/or enhance cell division rates. The above-mentioned application further relates to a method for improving the growth of plants by overexpression of APC10 gene and/or its variants or repression of the SAMBA gene and/or its variants. The genes whose activities are changed in patent application EP2391642 are distinct and regulate, in cell cycle, processes other than those presented herein.

BRIEF SUMMARY

The plants, techniques, and methodology described herein are capable of promoting an increase in the growth of a plant as a whole, leading to an increase of biomass and seed yield, the effects being visible in organs such as leaf, stem, root, and fruit production. In parallel, also provided are methods and means of increasing plant drought tolerance, generating plants better adapted to the environmental changes, improving their growth, biomass and yield.

Described herein is methodology to regulate cell cycle rates by modulating the expression and function of the AIP10 protein, encoded by the AIP10 gene, which participates in the ABAP1 regulatory network that is composed by members of the DNA replication machinery, transcription factors and other classes of proteins, so that there is an increase in plant biomass and plant yield. Furthermore, the modulation of AIP10 levels also increases tolerance of plants to drought.

Meanwhile, the incorporated EP Patent Application EP 2391642 relates to a process for increasing plant growth by overexpression of the gene APC10, which is a subunit of the APC/C complex and which, in turn, is one of the mitotic cycle regulators. Furthermore, the above-mentioned patent application describes a method of plant growth through suppression of the gene that produces the SAMBA protein, which is a protein that regulates the activity of APC10 protein, which is not addressed herein.

Moreover, none of the disclosures cited reached the same positive results in increasing seed productivity, enlarged organs such as leaf, stem, root, fruit production as well as increased drought tolerance, as described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 2A) Phenotype of plants 23 days after germination (DAG). (FIG. 2B) Graphical representation of the average values of fresh weight of shoots from plants 23 DAG. Error bars indicate average±standard deviation, n>10. A statistical analysis was performed by t-test (p-value <0.05). Asterisks (*) indicate significant changes between samples. The results demonstrate that the method of this disclosure leads to an increase in plant biomass.

(FIG. 3A) Images of aip10-1 and aip10-2 mutant plants (13 DAG) 6 days without water, compared to control wild-type plants (AIP10WT.1). Mutant aip10 plants show an increased growth compared to wild-type plants. (FIG. 3B) Images of aip10-1 and aip10-2 mutant plants (19 DAG) 12 days without water, compared to control wild-type plants (AIP10WT.1). The images show that aip10 mutant lines tolerate better drought than wild-type plants. (FIG. 3C) Graphical representation of the average values of fresh weight of shoots from well-watered plants (WW) 23 DAG. The results demonstrate that the method of this disclosure leads to an increase in plant biomass. (FIG. 3D) Graphical representation of the average values of fresh weight of shoots from 23DAG plants that were watered after being submitted to 12 days of water deficit (WD). Error bars indicate average standard deviation, n>10. A statistical analysis was performed by t-test (p-value <0.05). Asterisks (*) indicate significant changes between samples. aip10-1.1 and aip10-1.2 are batch of seeds coming from different aip10-1 plants. aip10-2.1 and aip10-2.2 are batch of seeds coming from different aip10-2 plants.

(FIG. 4A) Images show the phenotypical differences in the growth of soybean and cotton plants with reduced levels of AIP10 transcripts. Left side: NT plants; Right side: RNAi plants. (FIG. 4B) Images show the phenotypical differences in the growth of soybean plants with reduced levels of GmAIP10 transcripts. Left side: NT plants; Right side: RNAi plants.

FIGS. 9A-9H: Binary vector design based on RNA interfering strategies, successful soybean (*Glycine max*) genetic transformation, and promising phenotype of the improved plant growth and development in greenhouse conditions. The binary vectors for the (FIG. 9A) overexpression of the dsRNA construct which simultaneously target the soybean Glyma.07G021400.1, Glyma.07G021400.2, and Glyma.08G220400.1 genes (materials and methods and sequence listing), and (FIG. 9B) overexpression of the artificial miRNA (amiRNA; pre-miRNA sequence containing the specific soybean miRNA to targeted GmAIP10 genes) construct which simultaneously target also the same three soybean genes were synthesized in Epoch Life Science facilities and cloned in *E. coli* strain DH5α and *A. tumefaciens* strain GV3101. Soybean embryos from pre-germinated seeds of cultivar BRS284 were isolated and submitted to genetic transformation mediated by biolistic or *A. tumefaciens* combined with biolistic (agrolistic method).

Embryos submitted to genetic transformation were in vitro fortnightly subcultured and selected in magenta containing culture medium MS using as selective agent the commercial herbicide Imazapyr ARSENAL®NA (BASF®, Germany). Rooted and herbicide-resistant soybean plants conferred by the acetohydroxyacid synthase (ahas) selection marker were acclimated in pots containing the soil/substrate mixture and maintained in a greenhouse for one week. Then, acclimated plants were transferred to higher pots containing soil. The transgene insertion was checked by conventional PCR using specific primers for the bialaphos (bar) selection marker gene and the QIAGEN Multiplex PCR Kit (Cat No/ID: 206143, Qiagen), confirming the achievement of several independent events from both strategies used (specifically eight events for amiRNA strategy). For this, genomic DNA from young leaves was isolated according to Dellaporta et al. (1983) or using the DNeasy Plant Mini Kit (Qiagen). The DNA concentrations were estimated using a spectrophotometer (NanoDrop 2000, Thermo Fisher Scientific, Massachusetts, USA) and integrity was evaluated by 1% agarose gel electrophoresis. Eventually, the soybean plants were also screened using Enzyme-Linked Immunosorbent Assay (ELISA) assays with Anti-bar antibody::Rabbit Streptomyces hygroscopicus Phosphinothricin N-acetyltransferase Polyclonal Antibody (MBS1491343; conjugate with HRP). After advanced of the $T_0$ to $T_1$ generations, four events with the artificial miRNA (amiRNA) construct (Ev32, Ev18, Ev39, and Ev3) were chosen for preliminary molecular characterization based on conventional PCR (FIG. 9C) using primers for the Bar gene present in the transgene. Soybean seeds from four events, additional to non-transgenic (NT) plants, were initially germinated in Germitest® paper after incubation at 37° C., transplanted in pots containing 7 kg of soil/substrate mixture, maintained in a greenhouse, and screened by conventional PCR using primers for Bar gene as described above. Then, transgenic plants were weekly evaluated for plant vegetative development (FIG. 9D) and plant growth rate over time (days after planting) (FIG. 9E) from biometric analysis focused to the stages of the opening of the first, second and fourth trifoliolate leaf, and beginning of flowering compared to two non-transgenic lines (NT1 and NT2). After biometric analysis of plant development and growth, the same plants were evaluated for the pods and seed yield based on the number of pods per plant and total weight of seeds produced per plant (FIG. 9F) in transgenic plants of each event compared with NT1 and NT2 plants. Error bars represent confidence intervals corresponding to thirteen to seventeen biological replicates (each biological replicate corresponds to one plant). Asterisks indicate significant differences based on Tukey's test at 5%. (FIG. 9G) Plant status of 5 events from AIP10 amiRNA strategy in the T1 generation, showing a boost in growth and biomass production in soybean. (FIG. 9H) Soybean dsRNA AIP10 plants, showing an increase in the number of emerging flower buds.

FIG. 10: sequence alignments of the respective AIP10 amino acid sequences of corn, cotton, and soy. SEQ ID NO. references are indicated in the figure (left). Conserved regions (SEQ ID NO: 39 and SEQ ID NO: 40) are highlighted in bold. Underlined are amino acids $X_1$ and $X_2$, which vary in sequences SEQ ID NO: 41 and SEQ ID NO: 42.

DETAILED DESCRIPTION

Figure 1:
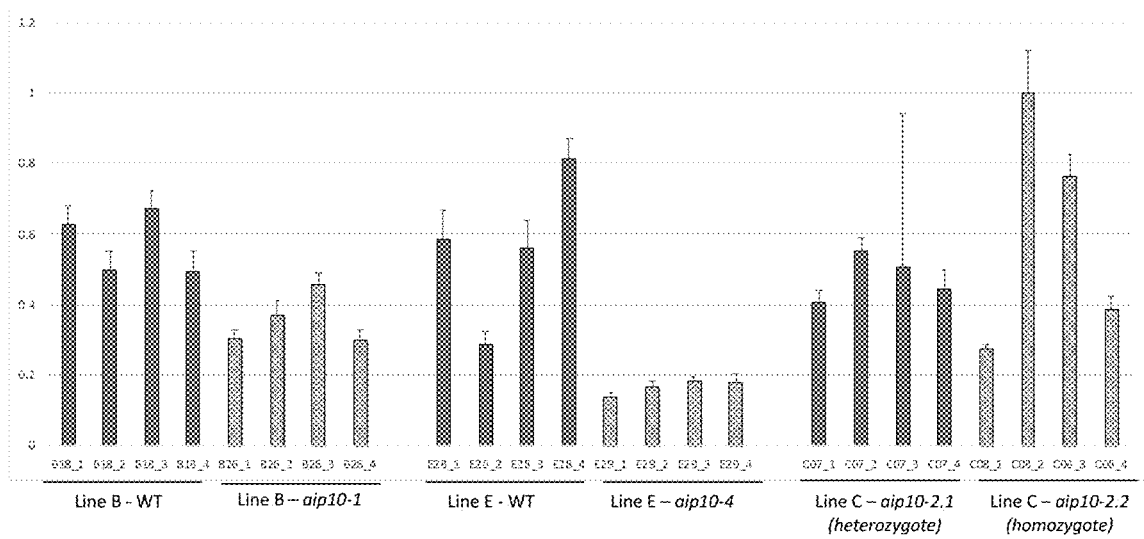
FIG. 1: Graphical representation of the average values of AIP10 mRNA levels in leaves of 15 days after germination (DAG) maize plantlets. AIP10 mRNA levels were quantified by qRT-PCR and normalized by 18S mRNA levels. Data shown represent average values obtained from independent amplification reactions (n=3) of individual plants. Bars indicate average±standard deviation of technical replicates.
Figure 2A:
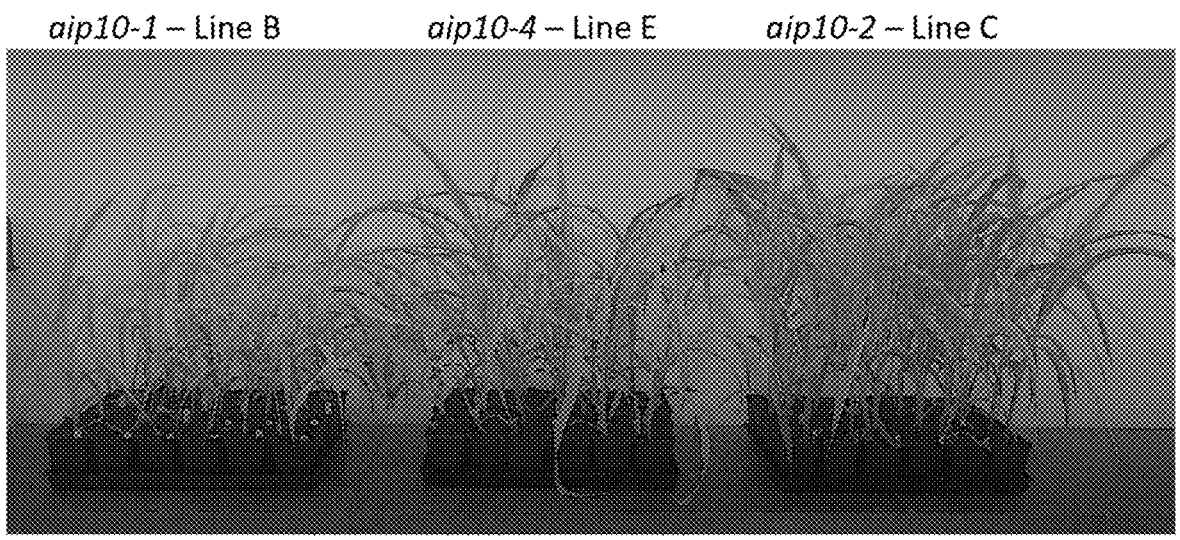
FIGS. 2A and 2B: Increased shoot biomass in different AIP10 CRISPR lines. Seeds were pre-germinated in paper rolls with water and kept in dark for three days, when seedlings at the same developmental stage were selected to be further analyzed. 7 days after pre-germination, seedlings were transferred to pots with soil and grown in the greenhouse.
Figure 2B:
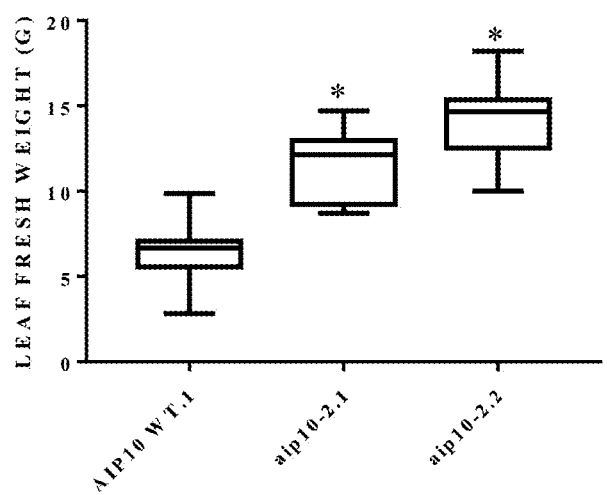
Figure 3A:
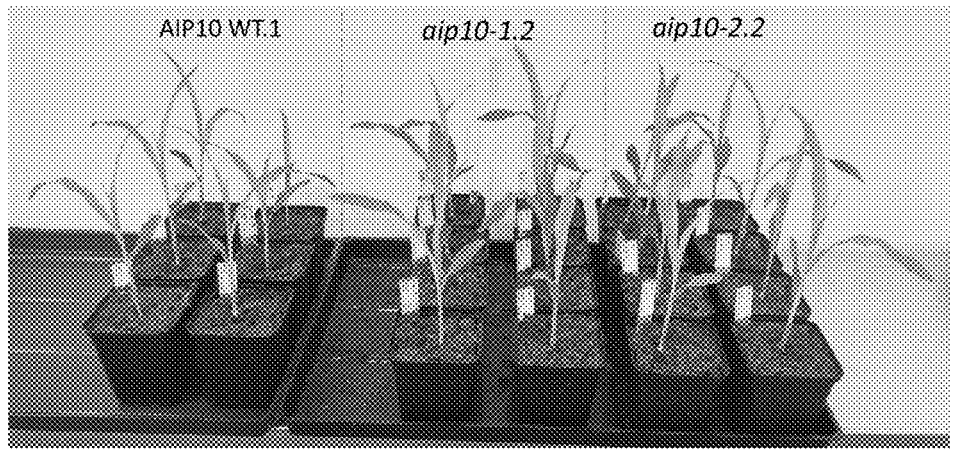
FIGS. 3A-3D: aip10 CRISPR mutant lines have increased shoot biomass and increased tolerance to drought. Seeds of AIP10WT.1 and aip10-1 and aip10-2 mutant lines were pre-germinated in paper rolls with water and kept in dark for four days, when seedlings at the same developmental stage were transferred to pots with soil and grown in the greenhouse. AIP10WT.1, aip10-1 and aip10-2 plants were divided in two groups: WW—normally watered plants; WD—water deficit plants. For the WD treatment, plants were watered twice with 50 ml water: a) when transferred to soil (4 DAG) and b) three days after (7 DAG). Afterwards, watering was suspended.
Figure 3B:
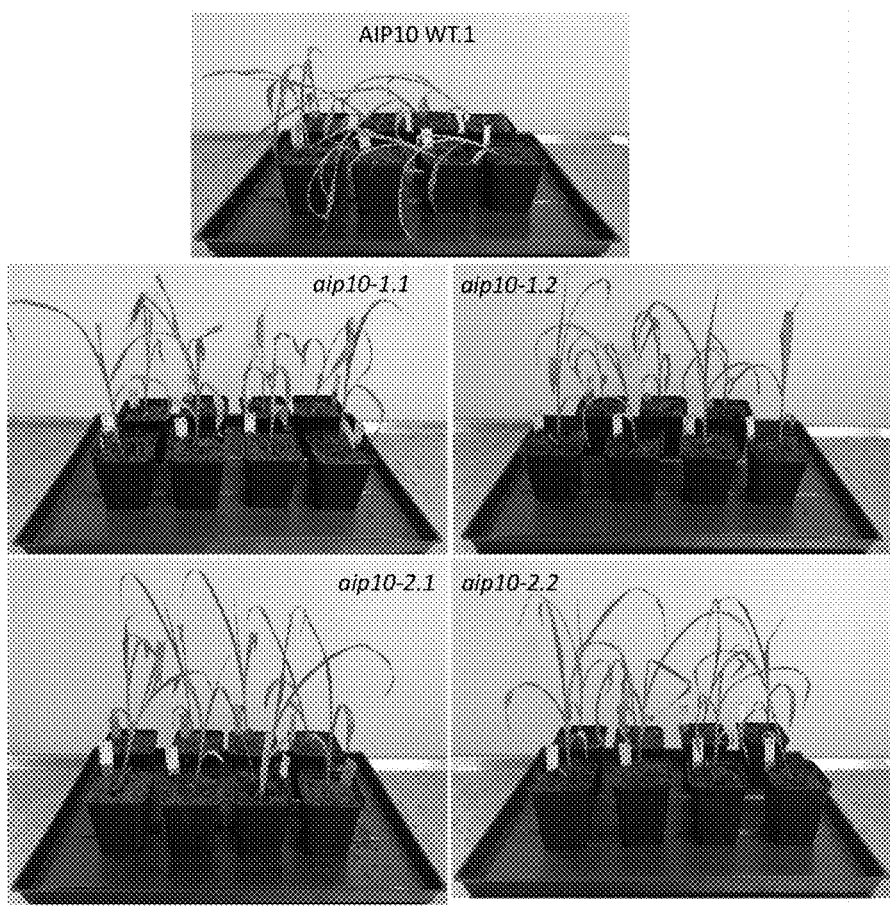
Figure 3C:
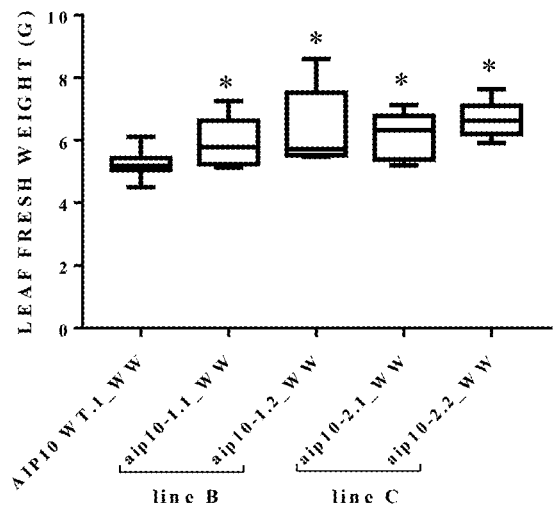
Figure 3D:
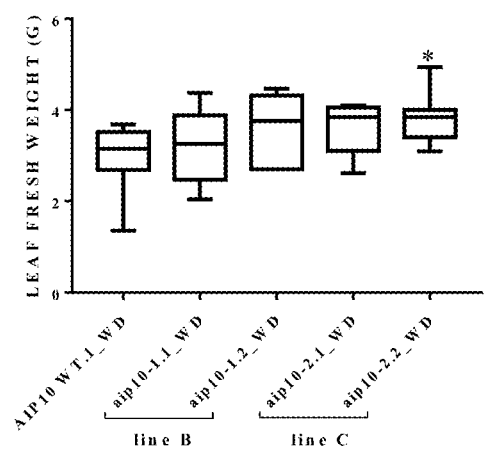
Figure 4A:
FIGS. 4A and 4B: Early development of transgenic cotton and soybean plants with reduced levels of AIP10 transcripts.
Figure 4B:
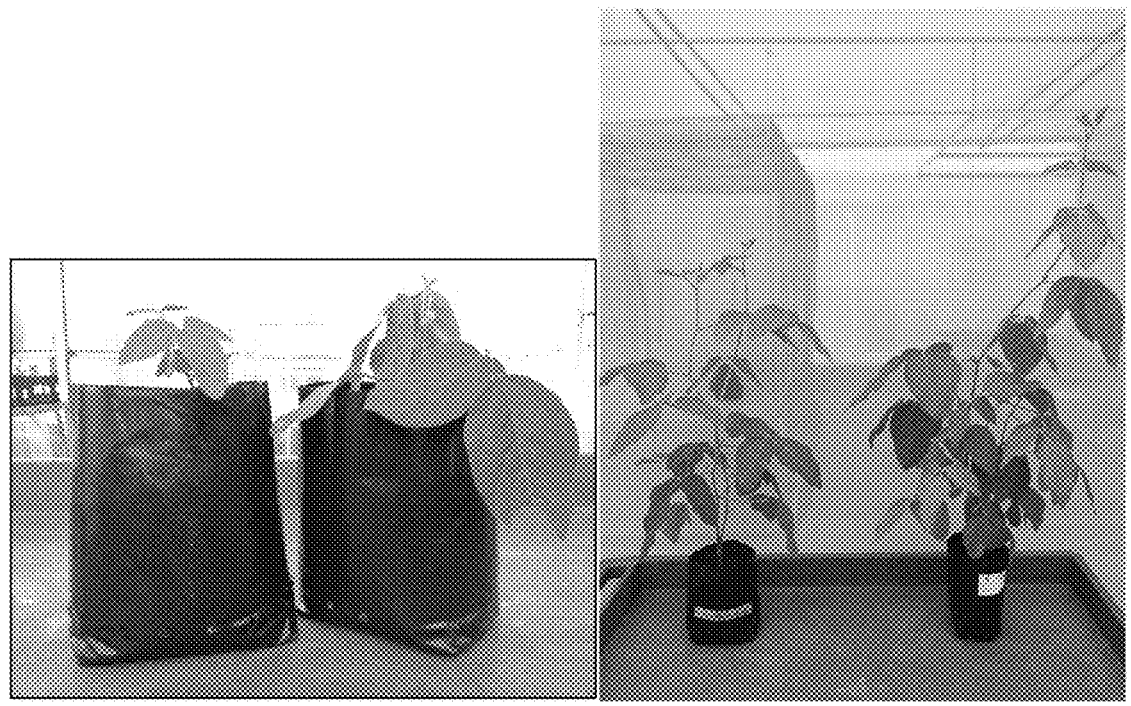

Described herein is the use of AIP10, or a variant thereof, to increase plant biomass and/or yield, and to increase drought tolerance. The use, as indicated here, is the use of the protein, and/or the use of a nucleic acid sequence (polynucleotide) encoding this protein, or the complement thereof.

The gene includes, but is not limited to, genomic DNA, cDNA, messenger RNA (including the 5' and 3' untranslated regions) and RNAi.

"Variants" as used herein, include, but are not limited to, homologues, orthologues and paralogues of SEQ ID NOS: 1, 19, 20, 21, 22, 23, 26, 27 and 28 (AIP10 coding sequences of corn (SEQ ID NO: 1), cotton (SEQ ID NOS: 19-23) and soybean (SEQ ID NOS: 26-28)).

Paralogues are genes within the same species that have originated through duplication of an ancestral gene; orthologues are genes from different organisms that have originated through speciation and are also derived from a common ancestral gene. Orthologues are genes from different organisms that have originated through speciation and are also derived from a common ancestral gene.

Preferably, the homologue, orthologue or paralogue has a sequence identity at polypeptide levels of at least 50%, 51%, 52%, 53%, 54% or 55%, 56%, 57%, 58%, 59%, preferably 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89% most preferably 90%, 91%, 92%, 93%, 94%, 95%, 96%, 97%, 98%, 99% or more when compared with SEQ ID NOS: 30, 31, 32, 33, 34, 35, 36, 37 and 38, aligned or not, as measured using genomic analyses tools as, but not limited to, the programs BLASTp, Clustal and COBALT.

Increase of plant growth and/or yield is measured by comparing the test plant, comprising a gene used according to the method of this disclosure, with the parental, non-transformed plant, grown under the same conditions as control. Preferably, increase of growth is measured as an increase of biomass production. "Yield" refers to a situation where only part of the plant, preferably an economical important part of the plant, such as the leaves, roots or seeds, is increased in biomass.

The term "biomass" as used herein means an increase in weight/mass of certain parts of the plant and can result from an increase in the area and/or increase in the quantity of this part of the plant.

The term "increase" as used herein means at least a 5%, 6%, 7%, 8%, 9% or 10%, preferably at least 15% or 20%, more preferably 25%, 30%, 35% or 40% more yield and/or growth in comparison to control plants as defined herein. Increase of plant growth, as used herein, is preferably measured as increase of any one or more of leaf biomass, root biomass and seed biomass.

Increase of plant drought tolerance is measured by comparing the test plant, comprising a gene used according to the method of this disclosure, with the parental, non-transformed plant, grown under the same conditions as control.

The term "increase in plant drought tolerance" as used herein means that test plants are able to support longer periods in soils with deficit in water availability, producing higher yields than the parental, non-transformed plant, grown under the same conditions. The term "increase" as used herein means at least a 5%, 6%, 7%, 8%, 9% or 10%, preferably at least 15% or 20%, more preferably 25%, 30%, 35%, 40%, 45% or 50% more yield and/or growth under drought conditions in comparison to control plants as defined herein.

In this disclosure, normal AIP10 protein expression and function is repressed or completely eliminated. Repression refers to the expression in the modified plant, compared with the non-modified parental plant, grown under the same conditions, and means a reduction or complete elimination of the mRNA levels and normal protein levels and function of the target gene or variants. Plant cells with loss of normal expression and function of AIP10 protein can be realized (or plants or plant cells which lack functional wild type AIP10 protein by means of a silencing construct directed to the AIP10 mRNA, or an artificial microRNA directed to the AIP10 mRNA or by gene disruption caused by a genome editing construct directed to the AIP10 gene), as a non-limiting example, by gene silencing, antisense RNA, RNAi, artificial microRNA, methodologies of genome editing (ZFN—"zinc-finger nucleases," TALENs—"transcription activator-like effector nuclease," CRISPR-Cas, and others), T-DNA insertion, transposons and others.

Design of RNAi, antisense RNA and genome editing by CRISPR is known to the person skilled in the art. As a non-limiting example, RNAi and CRISPR can be designed with tools available on the internet. The RNAi and CRISPR genome editing can be directed against a part of the 5' untranslated terminal region, against a part of the coding sequence, and/or against the 3' terminal region of the mRNA. Some non-limiting examples of target sequences are: SEQ ID NOS: 1, 19, 20, 21, 22, 23, 26, 27 and 28 of the Sequence Listing.

Also described herein are genetically modified plants, containing RNAi, or another method to decrease or eliminate normal AIP10 protein expression and function, against a nucleic acid encoding AIP10 or a variant thereof, as defined above, to increase plant growth, biomass and tolerance against drought stress. This RNAi and CRISPR genome editing will target only a part of the nucleic acid, whereby the target sequence can be situated in the coding sequence, or in the 5' or 3' untranslated regions of the nucleic acid encoding AIP10 or variant.

A "genetically modified plant," as used herein, is a plant which genome was modified by a recombinant DNA construct and/or by genome editing, in which the referred recombinant DNA can be introduced directly by transformation or indirectly by inbreeding or crossings.

The RNAi against a nucleic acid encoding AIP10 or a variant thereof, or another method to decrease or eliminate gene expression, as defined above, means that the method is able to decrease or eliminate the expression of AIP10 or a variant in a non-modified parental plant.

Repression of expression of a target gene can be obtained by transfer of a genetic construct. The transfer of foreign genes into the genome of a plant is called transformation. Transformation of plant species is a fairly routine technique known to the person skilled in the art. Advantageously, any of several transformation methods may be used to introduce the gene of interest into a suitable ancestor cell.

The methods described for the transformation and regeneration of plants from plant tissues or plant cells may be utilized for transient or for stable transformation.

Transformation methods include, but are not limited to, *Agrobacterium*-mediated transformation, "floral dip," the use of liposomes, electroporation, chemicals that increase free DNA uptake, injection of the DNA directly into the plant, particle gun bombardment, transformation using viruses or pollen and microprojection.

Preferably, the plants used in the method of this disclosure are from the group of commercially cultivated crop plants. The term "commercially cultivated crop plants" as used herein means plants belonging to monocot, dicot and eudicot families, traditionally used in the agriculture, preferably, but not limited to: maize, soybean, cotton, sugarcane, sorghum, wheat, barley, millet, rye, oats, cocoa, beans, rice, oilseed plants, grape, tomato, cassava, castor bean, papaya and poplar.

Described is a method of increasing plant biomass, plant yield and/or plant drought tolerance involves, but is not limited to: plant growth, RNA extraction, DNAse treatment, cDNA synthesis and cloning in plant expression vector, plant transformation and generation of genetically modified plants with the RNAi construct against AIP10 or variant, or another method to decrease or eliminate gene expression, as defined above.

Described herein are methods of utilizing (e.g., by down-regulating or reducing the expression of AIP10 protein and function) encoded by the AIP10 gene (or a variant thereof) in a plant, so as to promote increased biomass, plant yield, and/or to promote plant drought tolerance. In such a use, the AIP10 may comprise a polynucleotide consisting of members of the list SEQ ID NOS: 1, 19, 20, 21, 22, 23, 26, 27 and 28 or a variant of either thereof. When a variant is used that is a homologue, or orthologue or paralogue variant of AIP10, it may have a sequence identity at the polynucleotide level of preferably at least 50%, 51%, 52%, 53%, 54%, 55%, 56%, 57%, 58%, 59%, 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89%, preferably more than 90%, 91%, 92%, 93%, 94%, 95%, 96%, 97%, 98%, 99% or more, when compared to SEQ ID NOS: 1, 19, 20, 21, 22, 23, 26, 27 or 28. Such use may take place in a plant species such as corn, cotton or soybean any other species such as those selected from the group consisting of monocot, dicot, and eudicot, particularly commercially cultivated plants, preferably, but not limited to: maize, soybean, cotton, sugarcane, sorghum, wheat, barley, millet, rye, oats, cocoa, beans, rice, grape, tomato, cassava, castor bean, papaya, poplar, and/or others.

RNA Extraction

The collected plant material was immediately frozen in liquid nitrogen and stored in a freezer at −80° C. For RNA extraction, the material was macerated in liquid nitrogen and rapidly transferred to 1.5 ml microtubes containing 500 uL of TLE buffer (200 mM Tris-Cl, 100 mM LiCl, 5 mM EDTA, 1% SDS, pH 7.5) 250 μL 250 μL of phenol and chloroform. The microtubes were stirred for 1 minute and centrifuged at 12000 g for 20 minutes at 4° C. After centrifugation, the aqueous phase was transferred to microcentrifuge tubes and was added to one volume of chloroform: isoamyl alcohol (24:1). The new mixture was stirred for 1 minute and centrifuged at 20000 g for 15 minutes at 4° C. The aqueous phase was transferred to microcentrifuge tubes and 1 volume of 6 M LiCl with diethyl pyro-carbonate (DEPC) 0.1% was added. The tube was shaken for 1 minute and kept at 4° C. for 16 hours. The next day, tubes were centrifuged at 12000 g for 20 minutes at 4° C., the supernatant discarded and the precipitate solubilized in 1 ml 3M LiCl, DEPC 0.1%. The tubes were again centrifuged at 12000 g for 20 minutes at 4° C., the supernatant discarded and the precipitate solubilized in 250 μl H$_2$O with 0.1% DEPC. 1/10 volume of 3 M NaOAc pH 4.8 with 0.1% DEPC and 2 volumes (considering the amount of added NaOAc) of absolute ethanol were added to these samples. The samples were homogenized and incubated for 30 minutes at −80° C. or for 2 hours at −20° C. After incubation, the tubes were again centrifuged at 12000 g for 20 minutes at 4° C., the supernatant was discarded and the precipitate was washed with 1 mL of 70% ethanol with 0.1% DEPC. Again, the tubes were centrifuged at 12000 g for 20 minutes at 4° C., the supernatant was discarded and the precipitated RNA was solubilized in 20 µl H$_2$O with 0.1% DEPC.

DNAase Treatment

Total RNAs were treated with DNase I (New England Biolabs) to eliminate any contamination with genomic DNA. 0.5 U of DNAse I was used for each 1 µg of total RNA in enzyme buffer (200 mM Tris-Cl pH 8.3, 500 mM KCl, 25 mM MgCl2, 0.1% DEPC). RNAs were incubated with buffer and DNAse at 37° C. for 15 minutes. The RNA was purified by adding 1 volume of phenol, the phases were mixed by vortexing and then centrifuged at 20000 g for 10 minutes. The aqueous phase was transferred to a fresh tube to which was added 1 V of chloroform. A new centrifugation at 20000 g for 10 minutes was carried out and the aqueous phase was transferred to a new tube. The RNA was then precipitated by adding 1/10 V 3 M NaOAc 0.1% DEPC and 2 V of absolute ethanol, followed by incubation at −80° C. for 20 minutes, and centrifuged at 20000 g for 20 minutes. The supernatant was discarded and the precipitated RNA was washed with a solution of 70% ethanol with 0.1% DEPC, after which it was solubilized in MILLI-Q@ water with 0.1% DEPC.

cDNA Synthesis

After treatment with DNAse, the first strand cDNA was synthesized using the SUPERSCRIPT® III reverse transcriptase with total RNA samples (Invitrogen). The following protocol enables cDNA synthesis in a reaction where there is a range of 10 ng to 5 µg of total RNA. It was added into a microtube of 0.5 ml: 1 µL oligonucleotide Oligo (dT)20 (50 mM); 10 ng-5 µg of total RNA; 1 µL dNTP (10 mM) and the volume was complete with sterile distilled H$_2$O to 13 µL. The mixture was heated at 65° C. for 5 minutes and incubated on ice for 1 minute. After, 4 µL of 5× First-Strand Buffer (Buffer first tape); 1 µL DTT (0.1 M); 1 µL of RNAseOUT Recombinant RNase Inhibitor (40 U/µL) and 1 µL of SUPERSCRIPT® III (200 U/µL) were added to the microtube. The reaction was incubated at 50° C. for 60 minutes and then inactivated at 70° C. for 15 minutes. To remove remaining RNA, 2 U of RNaseH (USB, Affymetrix) were added to the microtube, and it was incubated at 37° C. for 15 minutes.

cDNA Synthesis for RT-PCR Analysis in Real Time

The first strand cDNA was synthesized using the kit "TAQMAN® First strand cDNA synthesis" and it was performed in reactions with a final volume of 25 µL, according to the manufacturer. For each reaction, 500 ng of total RNA were added plus 2.5 µl 10×TAQMAN® RT buffer, 25 mM of MgCl2 5.5 µl, 5 µl dNTPs Mix, 1.25 µl of random hexamer, 0.5 µl RNase inhibitor, 0.625 µl of MULTISCRIBE™ Reverse Transcriptase (50 U/µl). The samples were incubated at 25° C. for 10 minutes, followed by 48° C. for 30 minutes and a final step at 95° C. for 5 minutes. Samples were diluted four times with 10 mM Tris-Cl pH 8.0 and stored at −20° C. or used immediately.

Biomass and Productivity of the Reproductive Part

Measurements of height, silique production and seed yield were made with AIP10 knockout plants and RNAi-AIP10, and compared with control plants.

The height of the main axis of the plants was measured with the aid of a measuring tape and the number of siliques produced was counted throughout the development. Data were statistically analyzed and considered different (t-test).

The production of seeds of each plant was individually evaluated. Seeds were collected, and the total number of seeds produced by each individual was weighed on a precision scale and the values obtained were analyzed and considered statistically different (t-test).

Tolerance to Drought Stress

To evaluate the tolerance to water stress, plants were cultivated and watered normally for 25 days. Then watering was suspended for 7 days in a group of plants, and for 12 days in the other group. After this period, watering was resumed and after 7 days, plant survival rate was evaluated. At the end of development, the number of siliques produced by each individual was counted. Data were statistically analyzed and considered different (t-test).

Results

1. Generation of Maize AIP10 Mutants by CRISPR-Cas9

We generated AIP10 CRISPR-Cas9 edited plants in the maize genotype B104 by using a dual gRNA approach (Xing H L et al (2014) *BMC Plant Biol.* 14, 327). The nucleotide sequence of the wild type maize coding region (CDS) is depicted in SEQ ID NO: 1. Two gRNAs were designed to target at exon1 and exon2 of maize AIP10, respectively, as depicted in SEQ ID NOS: 2 and 3. Primers were designed that matched with the dual sgRNA sequences:

Fw:
(SEQ ID NO: 4)
ATATATGGTCTCTGGCGACCTGGGGGATCAGCCGGAAGTTTTAGAGCTA

GAAATAGCAAGTTAAAATAAGG
and

RV:
(SEQ ID NO: 5)
TTATTGGTCTCTAAACTCCGCTTCTCGGATAGGTTATGCTTCTTGGTGCC

GC.

PCR was performed on the pCBC-MT1T2 plasmid, resulting in a fragment containing the desired target sites and the correct sites for ligation into the pBUN411-Sp destination vector using Golden Gate cloning. The expression vector was transformed in *Escherichia coli* strain DH5α and *Agrobacterium tumefaciens* strain EHA101. Maize embryogenic calli from genotype B104 were submitted to genetic transformation mediated by *A. tumefaciens* (Coussens G et al. (2012) *J. Exp. Bot.* 63, 4263-4273). Transgenic rooted shoots were confirmed by PCR analysis and transferred to soil, acclimatized in the growth chamber for several weeks and subsequently transferred to the greenhouse. At this stage, plants were screened by the phosphinothricin acetyl-transferase (PAT) assay (AgraStrip® LL Strip Test). Genome editing was checked by extracting genomic DNA of the leaf plantlets (Direct-zol™ RNA MiniPrep Plus from Zymo), followed by conventional PCR using specific primers for target1 (primers Aip0-F2: GGCCCAGAGCCACAA-GATAA (SEQ ID NO: 6); Aip10-R2 GCTTGTGGACCGAAACGAAG (SEQ ID NO: 7) and for target2 (primers Aip10-F5:CATCCTCGTCACTCGCTAAC (SEQ ID NO: 8); Aip10-R5 ACATGAACGCGTACTCTT-TATTATC (SEQ ID NO: 9), that specifically amplify genomic regions around the gRNAs binding. Genomic PCRs were performed using standard protocols, such as Gotaq DNA Polymerase, using the following reaction conditions: Annealing 60° C.*, 35 cycles, Extension 72° C. 1 min. The target1 and target2 PCR fragments were purified and sequenced (Eurofins Genomics). Eventually, genomic DNA PCR was performed to identify Cas 9 (primers: Cas9_FW2: CGAGATGGCGAAGGTTGACG (SEQ ID NO: 10), Cas9_RV4: AATGTCCGCTGCTTCCTCAG (SEQ ID NO: 11) using standard PCR protocols, such as Q5

DNA Polymerase), using the following reaction conditions: Annealing 68° C.*, 30 cycles, Extension 72° C. 40 seconds. Genome edited plants were crossed with B104 and self-pollinated. Heterozygote plants without Cas9 were selected in T1 (by genomic PCR and PAT assay) and were self-pollinated. In T2, wild-type and homozygote plants were selected, self-pollinated to generate WT and homozygote seeds for phenotypic analyses. After having advanced from the T0 to T1 generations, three maize mutant lines harboring different AIP10-CRISPR alleles were further analyzed (see Table 1). All of them showed premature stop codons at exon 1, indicating a knockout of the gene expression, by preventing the synthesis of the correct protein. In addition, aip10-2 showed a 24 bp deletion in the functional domain of the protein, in exon 2. AIP10 mRNA levels were quantified by qRT-PCR in leaves of plantlets of the three mutants (see FIG. 1). RNA was extracted with Direct-zol™ RNA Mini-Prep Plus (Zymo), cDNAs were prepared with qScript® cDNA SuperMix (QuantaBio). qRT-PCR reactions were performed using standard conditions. AIP10 mRNA was amplified with the primers qAip10f: CTTT-GAGCCCGCGTCGTA (SEQ ID NO: 12) and qAip10r: CGTCAGCCAGCTGCTTCT (SEQ ID NO: 13). The 18S gene was used as normalizing gene (primers 18s-f-qpcr: ACCTTACCAGCCCTTGACATATG (SEQ ID NO: 14) and 18s-r-qpcr: GACTTGACCAAACATCTCACGAC (SEQ ID NO: 15)). The results showed high levels of aip10-2 expression in Line C mutants, compared with the AIP10 levels in wild-type plants. Also, aip10-2 mutants have a deletion in the functional domain of the protein at exon 2, that has a methionine as a putative start codon. As untranslated mRNAs produced by genome editing have frequently been reported to be present in low levels in mutant plants, aip10-2 mutants possibly express a truncated dominant negative version of the AIP10 protein.

TABLE 1

AIP10 CRISPR mutants

| AIP10 alleles | gRNA1 | gRNA2 |
|---|---|---|
| aip10-1 (Line B) | A insertion | C insertion |
| aip10-2 (Line C) | T insertion | 24 bases deletion |
| aip10-4 (Line E) | −10 bases | T insertion |

2. Phenotypic Analysis of AIP10-CRISPR Lines

The effect of the three mutant aip10 lines on maize biomass was analyzed during early stages of plant growth. Seeds were pre-germinated in paper rolls with water, in the dark, and subsequently, seedlings at the same developmental stage were transferred to pots with soil, being cultivated at the greenhouse. In general, in different experiments, mutant lines C (aip10-2) showed the most pronounced phenotypes of increased shoot biomass, by measurements of leaf fresh weight of plants 23 days after germination (DAG) (see FIGS. 2A, 2B and 3A-3C).

Analyses of tolerance to drought stress were also performed during early stages of plant growth. The data showed that mutant lines B (aip10-1) and C (aip10-2) tolerated longer periods of drought than wild-type plants (see FIG. 3B). The results demonstrate that gene inactivation of the maize AIP10 gene leads to an increase in maize biomass and produces maize plants more tolerant to drought stress.

Figure 5:
FIG. 5: Binary vectors design based on RNA interfering strategies, successful cotton (*Gossypium hirsutum*) genetic transformation, and efficient downregulation of the endogenous GhAIP10 genes in transgenic events. The binary vectors carrying the strategies based on overexpression of the dsRNA (Panel A) and artificial miRNA (amiRNA; pre-miRNA sequence containing the specific cotton miRNA to targeted GhAIP10 genes) (Panel B) to target the GhAIP10 transcripts (see materials and methods and sequence listing) were synthesized in Epoch Life Science facilities (Missouri City, USA) and cloned in *Escherichia coli* strain DH5α and *Agrobacterium tumefaciens* strain GV3101. Cotton embryos from seeds of cultivar BRS372 were isolated and submitted to genetic transformation mediated by biolistic or *A. tumefaciens* combined with biolistic (agrolistic) as described by Rech E L et al (2008) *Nature Protocols* 3, 410-418). Embryos submitted to genetic transformation were in vitro cultivated in magenta containing MS medium and selected using as selective agent the commercial herbicide Imazapyr ARSENAL®NA (BASF®, Germany). Rooted and herbicide-resistant plants conferred by the acetohydroxyacid synthase (ahas) selection marker were acclimated in pots containing the soil/substrate mixture and maintained in a greenhouse. The transgene insertion was checked by conventional PCR using specific primers for the bialaphos (bar) selection marker gene and the QIAGEN Multiplex PCR Kit (Cat No./ID: 206143, Qiagen), confirming the achievement of several independent events (total of 29 events) from both strategies used (dsRNA and amiRNA). For this, genomic DNA from young leaves was isolated, according to Dellaporta et al. (1983) or using the DNeasy Plant Mini Kit (Qiagen). The DNA concentrations were estimated using a spectrophotometer (NanoDrop 2000, Thermo Fisher Scientific, Massachusetts, USA) and integrity was evaluated by 1% agarose gel electrophoresis. Eventually, the plants were also screened using a QuickStix for PAT/bar in cotton leaf & seed kit (EnviroLogix) or Enzyme-Linked Immunosorbent Assay (ELISA) assays with Anti-bar antibody::Rabbit *Streptomyces hygroscopicus* Phosphinothricin N-acetyltransferase Polyclonal Antibody (MBS1491343; conjugate with HRP). After advanced of the $T_0$ to $T_2$ generations, five events (E7.4, E12.5, E11.5, E7.3, and E2.4.2) were chosen for molecular and phenotype characterization (Panel C) in the greenhouse condition. The putative downregulation of the GhAIP10 gene in these events compared to wild-type (WT) and nontransgenic (NT) plants was evaluated using Real-time RT-qPCR assays using specific primers for the GhAIP10 gene (Gohir.A11G075200, Gohir.D11G079900.1, and Gohir.D11G079900.2). For this, total RNA was isolated using Concert™ Plant RNA Reagent (Invitrogen) from young leaves, and its concentration estimated using a spectrophotometer (NanoDrop 2000, Thermo Scientific, Massachusetts, USA) and its integrity evaluated with 1% agarose gel electrophoresis. RNA samples were treated with RNase-free RQ1 DNase I (Promega) according to the manufacturer's instructions. Then, 2 to 4 μg of DNase-treated RNA was used as a template for cDNA synthesis using Oligo-(dT)20 primer and SuperScript III RT (Life Technologies, Carlsbad, Calif., USA), according to the manufacturer's instructions. The cDNA was 10× diluted with nuclease-free water. The GhUb14 gene (Gohir.A10G015000) (Ribeiro T P et al (2020) *Biotechnology Research and Innovation*) was used as an endogenous reference for relative expression normalization. The qPCR reactions were performed with SYBR® Green master mix (Promega) in an Applied Biosystems 7500 Fast Real-Time PCR System (Applied Biosystems, USA) (Panel D). The conditions for qPCR included an initial 95° C. for 10 min, then 40 cycles of 95° C. for 15 s and 60° C. for 1 min, followed by a final melting curve analysis. Three to six biological replicates were used for each event, while each plant composed one biological replicate. All cDNA samples were carried out in technical triplicate, while primer efficiencies and target-specific amplification were confirmed by a single and distinct peak in the melting curve analysis. The relative expression level (Fold-change) was calculated using the $2^{-\Delta\Delta Ct}$ method (Schmittgen and Livak (2008) Nature Protocols 3, 1101). Error bars represent confidence intervals corresponding to three to six biological replicates. Asterisks indicate significant differences based on Tukey's test at 5%.
Figure 5:
Figure 5:
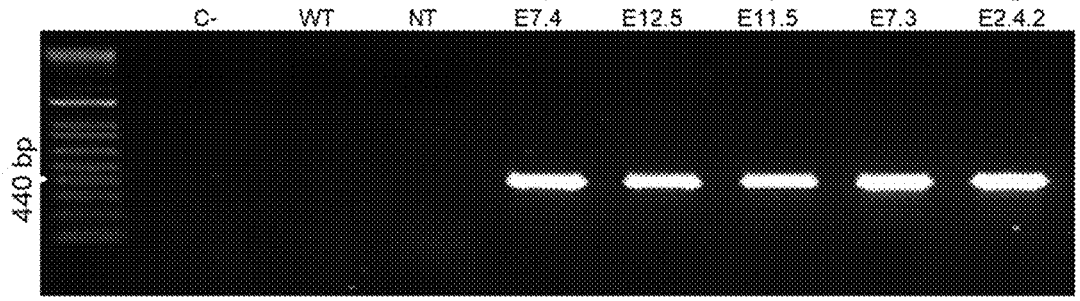
Figure 5:
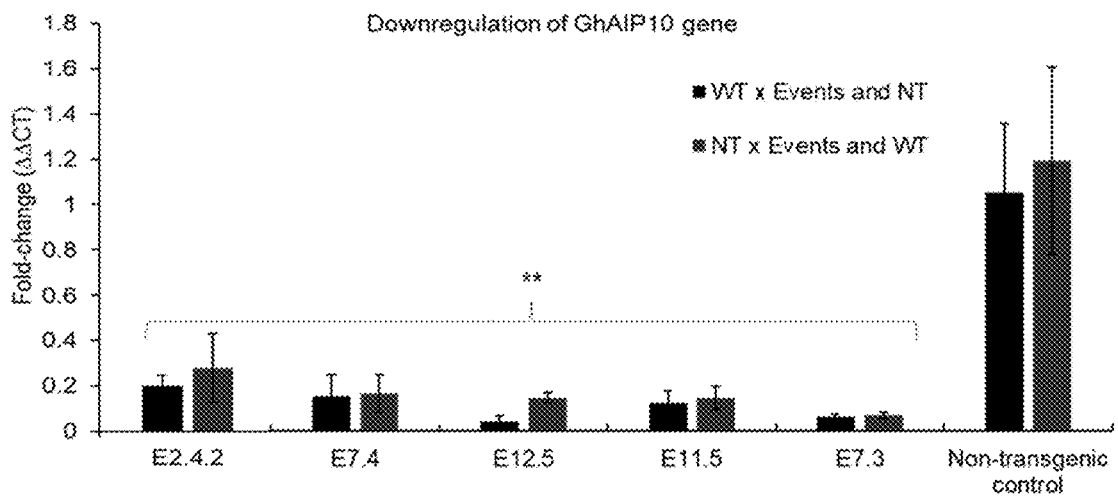
Figure 6:
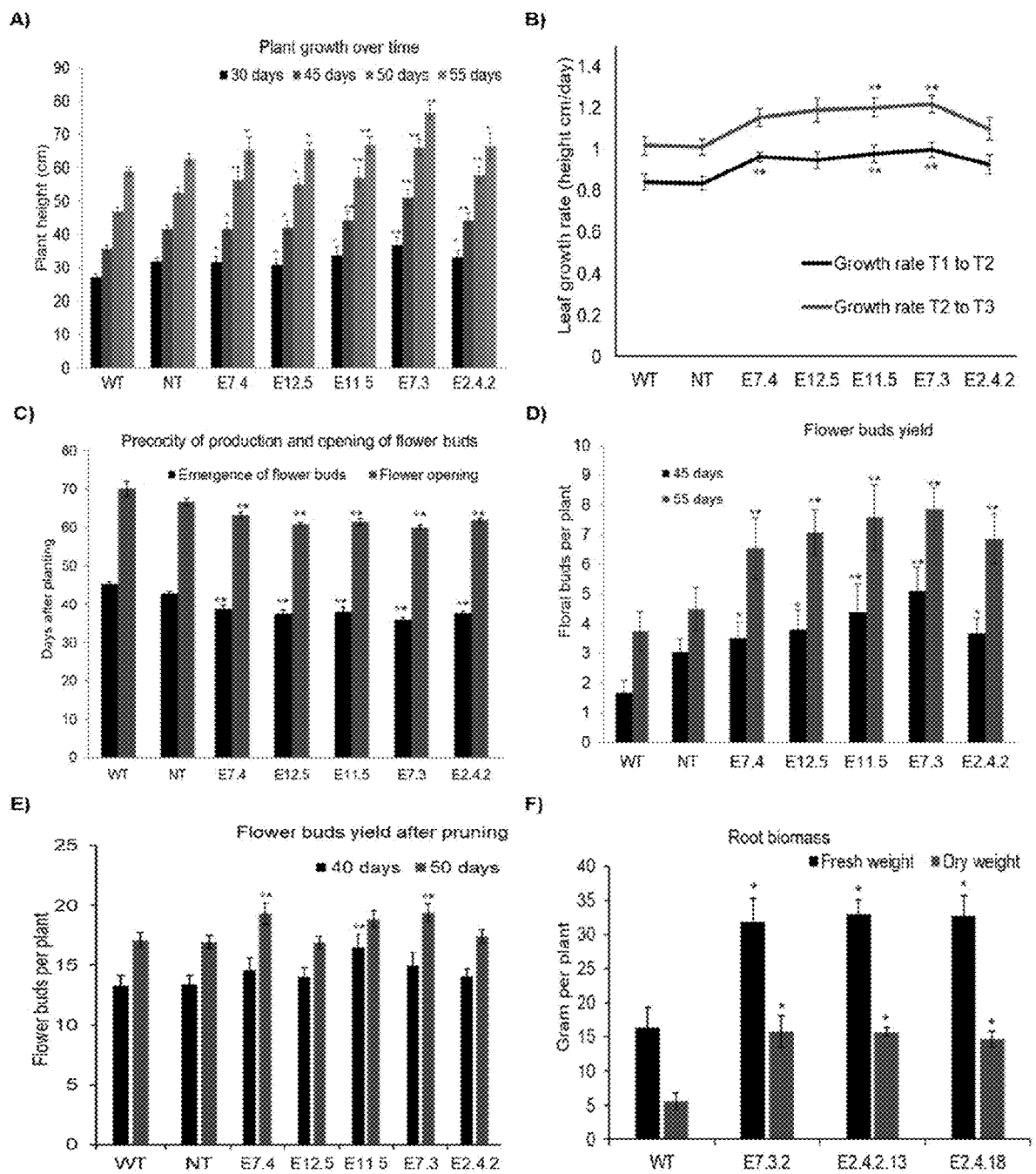
FIG. 6: Phenotyping of the cotton events in greenhouse conditions for the plant and leaf growth rate over time, precocity in the production and opening of flower buds, flower buds yield per plant, and root biomass yield. Cotton seeds from $T_1$ and $T_2$ events were initially germinated in Germitest® paper after incubation at 37° C., transplanted in pots containing soil/substrate mixture, maintained in a greenhouse, and screened by conventional PCR as described above. Transgenic plants were evaluated for plant growth rate over time (Panel A) from the biometric analysis performed at 30 to 55 days after planting comparing transgenic events with wild-type (WT) and non-transgenic (NT) plants. In addition, the leaf growth rate (Panel B) was determined from the youngest leaves from the top of the plant from time 1 (T1; 40 days after planting) to time 2 (T2; 43 days after planting), and time 3 (T3, 48 days after planting). The precocity of the transgenic events was determined based on the number of days after planting for the emergence and opening of the first flower buds (Panel C) compared to the WT and NT plants. The number of flower buds per plant (Panel D) was determined at 45 and 55 days after planting in transgenic events compared to the WT and NT plants. In addition, the flower buds yield was also determined at 45 and 55 days after the first pruning (Panel E) of the transgenic events compared to the WT and NT plants. Error bars represent confidence intervals corresponding to fifteen to eighteen biological replicates (each biological replicate corresponds to one plant). Asterisks indicate significant differences from WT (red asterisk) and NT (black asterisk) plants based on Tukey's test at 5%. The root biomass (fresh and dry weight) yield (Panel F) was determined in $T_2$ and $T_3$ events at the beginning of flowering and compared to WT plants. Cotton seeds from transgenic events and WT plants were initially germinated in Germitest® paper after incubation at 37° C., transplanted in pots containing soil, maintained in a greenhouse, and screened by conventional PCR as described above. Error bars represent confidence intervals corresponding to six to eight biological replicates (each biological replicate corresponds to one plant). Asterisks indicate significant differences from WT plants based on Tukey's test at 5%.
Figure 7:
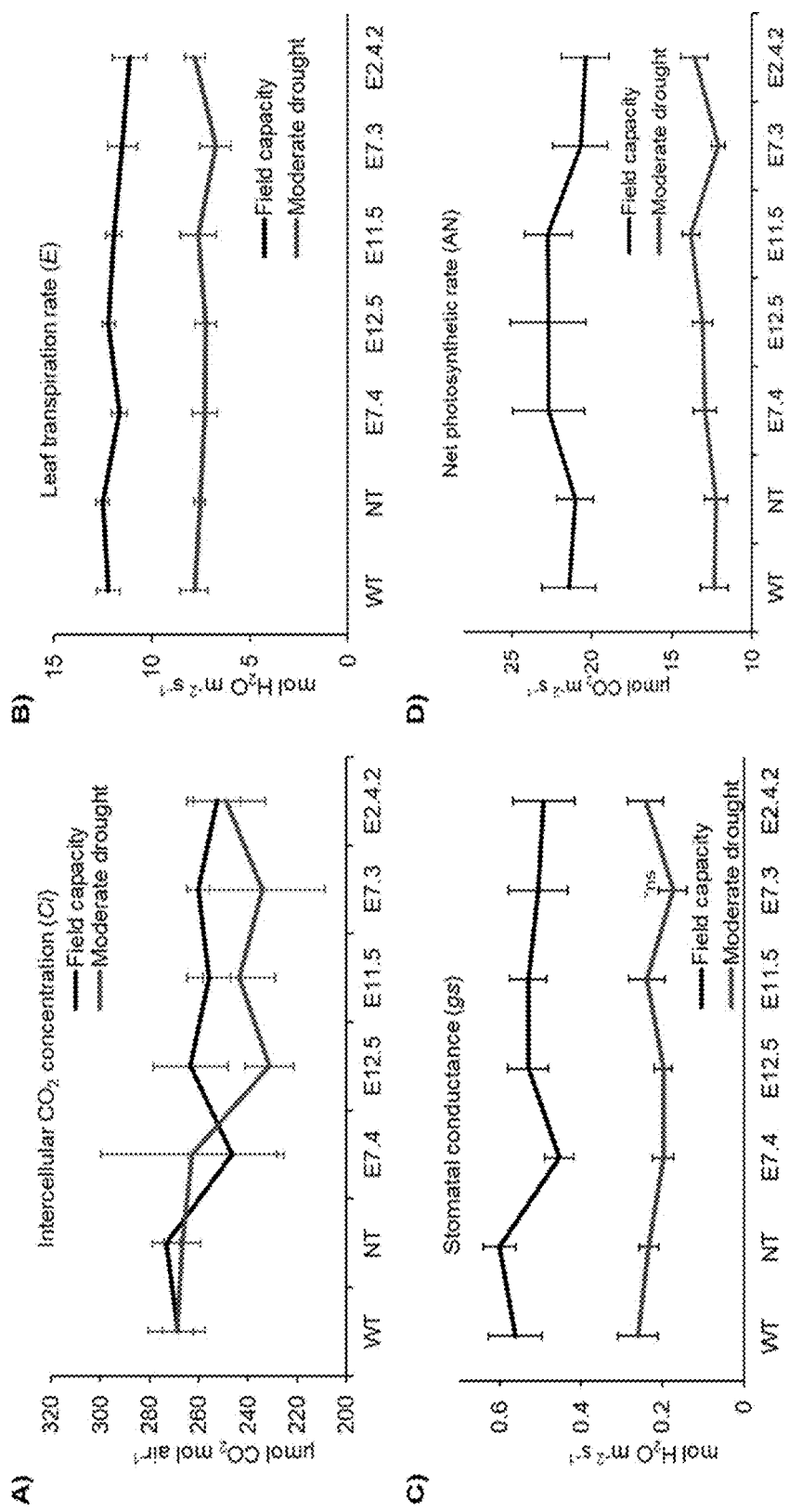
FIG. 7: Agronomic performance equivalent of the transgenic events compared to wild-type (WT) or non-transgenic (NT) plants when well-watered or exposed to the moderate drought stress in greenhouse conditions. For this, cotton seeds from $T_1$ and $T_2$ events, WT and NT plants were initially germinated in Germitest® paper after incubation at 28° C., transplanted in pots containing soil, maintained in a greenhouse and screened by conventional PCR as described above. Ecophysiological analysis were performed when plants reached the pre-flowering stage at 4 days after all plant groups achieved the desired water level of well-watered (−0.03 MPa) to moderate water deficit (−0.60 to −0.73 MPa). Soil moisture was monitored using the WP4C Dewpoint PotentiaMeter psychrometer (Decagon WP4, Pullman, Wash., USA). The trials were carried out in a randomized design with 7 to 10 biological replicates for each treatment (each replicate was composed of one plant). Gas exchange measurements were carried out using a portable conventional infrared gas analyzer system with a 6.25 cm² automatic leaf chamber (LCpro-SD; ADC BioScientific Ltd., UK). The photosynthetic photon flux density (PPFD) was fixed at 1500 μmol $m^{-2}s^{-1}$ using a red-blue LED light source built into the leaf cuvette. The intercellular $CO_2$ concentration (Ci) (Panel A), leaf transpiration rate (E) (Panel B), stomatal conductance ($g_s$) (Panel C), and Net photosynthetic rate ($A_N$) (Panel D) parameters were measured from the youngest leaves from the top of the plant. Significant differences from WT plants were checked with Tukey's test at 5%.
Figure 8:
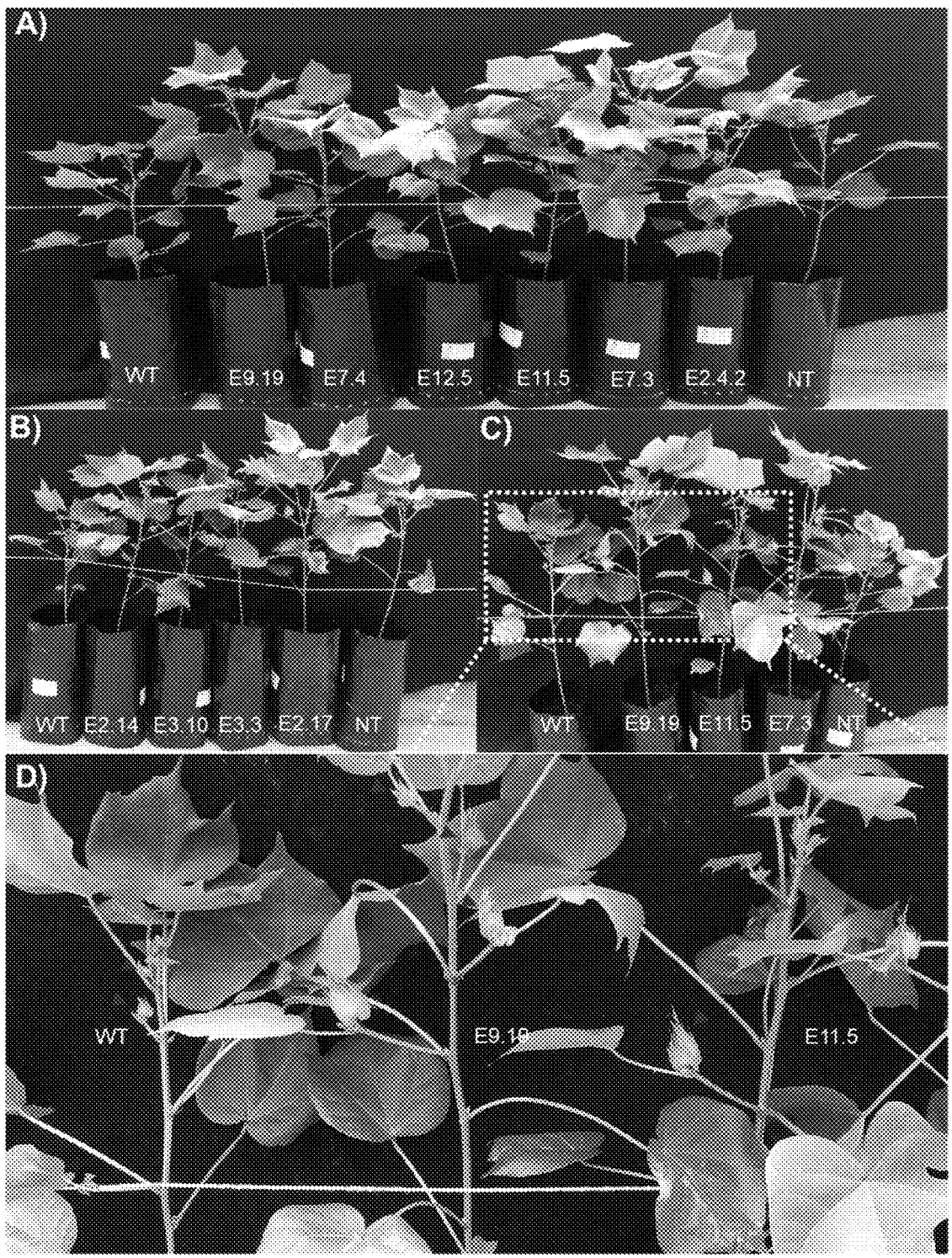
FIG. 8: Cotton plants 40 days after planting, showing higher plant growth (Panels A and B) and precocity in the emergence of flower buds (Panels C and D).

3. RNA Interference of the AIP10 Genes in Transgenic Cotton and Transgenic Soybean Plants It was previously shown that transgenic A. thaliana plants overexpressing a construct for triggering the post-transcriptional downregulation of the AthAIP10 gene transcripts showed significantly larger root system and leaves, improved plant growth, produced more seeds and were more tolerant to water deficit (see WO2015127521). Given these promising results in the model plant A. thaliana, transgenic plants of cotton and soybean were generated that resulted in the negative regulation of the respective endogenous AIP10 genes and the phenotype of these plants regarding the increase in biomass, precocity, productivity, and improvement in tolerance to water deficit were evaluated. Transgenic cotton and soybean plants cultivars BRS372 and BRS284, respectively, constitutively overexpressing a construct based on RNA interference (RNAi) were generated and characterized. A first strategy was based on a construction that results in the transcription of a long RNA capable of forming double-strand RNA (dsRNA) when after its processing in the cytoplasm resulted in a high accumulation of small interfering RNA (siRNAs) responsible for targeting and negatively regulating, at the post-transcriptional level, the endogenous AIP10 gene transcripts (see FIG. 5, Panel A, and FIG. 8, Panel A). A second strategy used was based on a construction that resulted in the transcription of an engineered RNA capable of forming dsRNA that after being processed in the cytoplasm results in a high accumulation of specific microRNA (miRNA) responsible also for targeting and negatively regulating, at the post-transcriptional level, the endogenous AIP10 genes (see FIG. 5, Panel B and FIG. 8, Panel B). Several independent events of the cotton (total of 29 events from both RNAi strategies) and soybean (several events with dsRNA and a total of eight events from amiRNA strategy) were generated from the genetic transformation of the embryos mediated by biolistic or agrolistic delivery method. After successive selection rounds in selective culture medium containing herbicide Imazapyr, resistant and rooted plants were acclimated in a greenhouse. Molecular assays based on conventional PCR using specific primers allowed to prove the insertion of the transgene in these events. Then, five and four independent events from cotton and soybean, respectively, were selected to further characterize the phenotype in greenhouse conditions (FIG. 5, Panel C, and FIG. 8, Panel C). Cotton $T_1$ and $T_2$ events carrying one to two transgene copies showed in both RNAi strategies used the efficient downregulation in the GhAIP10 genes, compared to non-transgenic plants (Table 2; FIG. 5, Panel D). In addition, some cotton events showed in greenhouse conditions improved plant growth over time (FIG. 6, Panels A and B), were 5 to 10 days more precocious compared to non-transgenic plants (FIG. 6, Panel C), showed higher flower buds yield (FIG. 6, Panels D and E), and increased root biomass production of the 30 to 40% (FIG. 6, Panel F). No penalty was observed in transgenic events under field-capacity (well-watered) or related to the moderate water deficit tolerance (FIG. 8, Panels A-D) and in cotton fiber properties (Table 2).

Figure 9G:
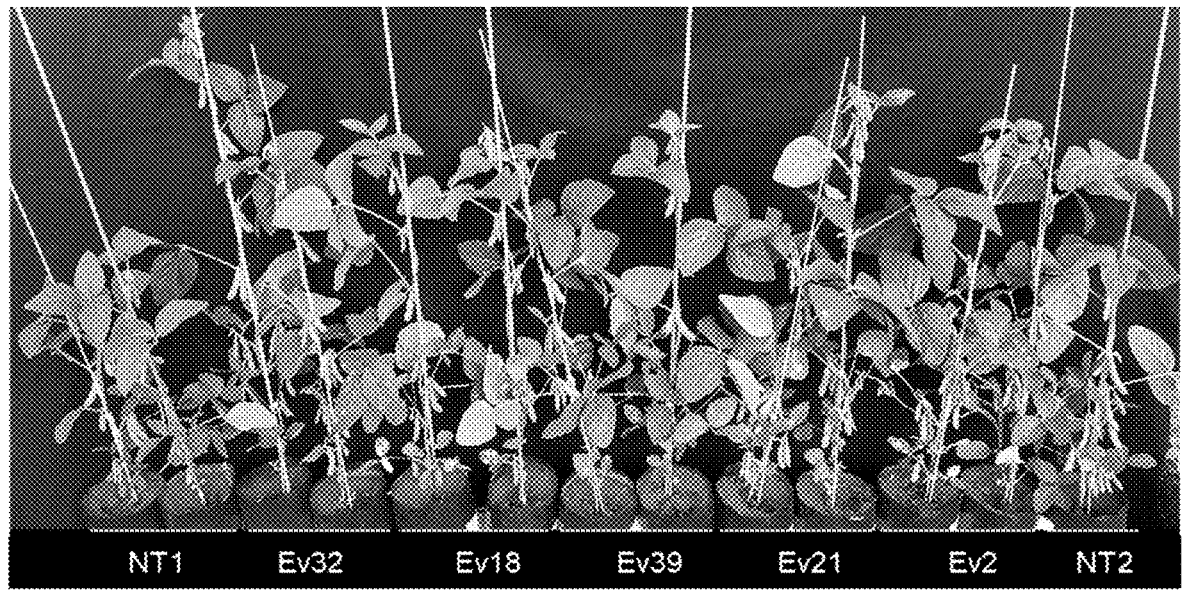
Figure 9H:
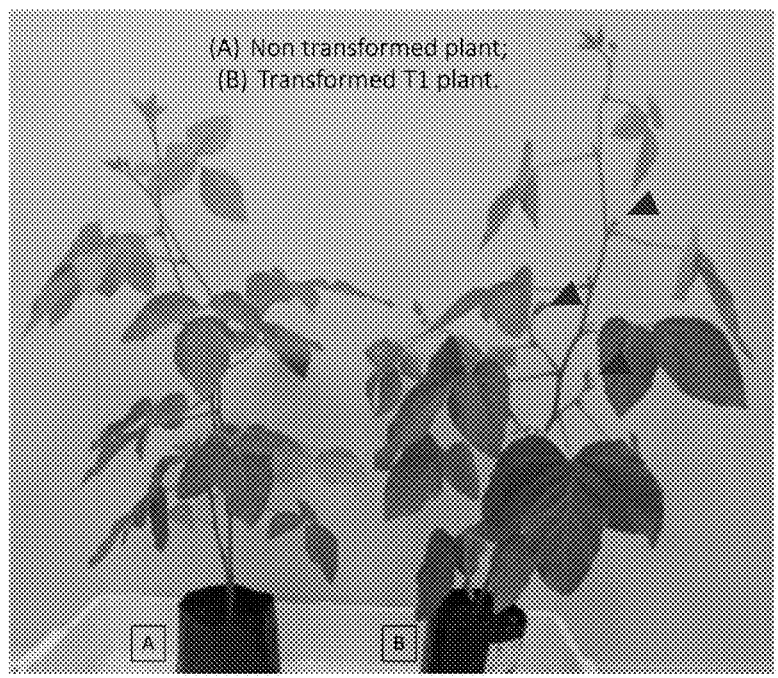

Similar to the cotton events, the soybean $T_1$ events with amiRNA constructs showed improved plant growth (FIGS. 9D and 9E), while the number of pods per plant and weight seeds per plant was increased in at least one event (FIG. 9F). Soybean $T_1$ events with dsRNA showed a significant increase in the number of pods and seeds production under greenhouse conditions (Table 4). These preliminary results obtained in the greenhouse conditions highlight the potential use of this target GmAIP10 genes and the biotechnological strategies used for its downregulation, aiming to improve agronomic characteristics in crops of economic interest. Phenotypic assessments are now being conducted in more advanced generations in order to evaluate more agronomic characteristics in the selected events. Field assays are being now conducted to evaluate the agronomic performance of the generated events.

TABLE 2

Transgene copy number in $T_1$ and $T_2$ cotton events determined by quantitative real-time PCR assays. For this, the genome DNA of cotton plants maintained in the greenhouse was isolated and purified from young leaves using the DNeasy Plant Mini Kit (Qiagen, Germany) according to the manufacturer's instructions. The concentration was determined using a spectrophotometer (NanoDrop 2000, Thermo Fisher Scientific, USA), and integrity was evaluated with 1% agarose gel electrophoresis. The copy number of the transgene integrated into the plant genome was estimated, according to Yang et al. (2012), using a qPCR-based $2^{-\Delta\Delta Ct}$ method using the Bar gene present in the transgene as the target. The copy number ratio of the transgene was obtained by the ratio between the absolute concentration of the transgene and the GhUBC1 (Gohir.A10G152900) endogenous reference gene (Ribeiro et al., 2020) in the respective sample.

| Strategy | Event | Plant generation | Copy number of transgene |
|---|---|---|---|
| dsRNA | E.2.4.2.1 | $T_2$ | 2 |
|  | E.2.4.2.13 | $T_2$ | 1 |
|  | E.2.4.2.18 | $T_2$ | 2 |
| amiRNA | E.7.3.2 | $T_1$ | 1 |
|  | E.7.3.5 | $T_1$ | 2 |
|  | E.7.3.7 | $T_1$ | 1 |
|  | E.7.4.3 | $T_1$ | 1 |
|  | E.7.4.7 | $T_1$ | 1 |
|  | E.7.4.18 | $T_1$ | 1 |
|  | E.11.5.4 | $T_1$ | 2 |
|  | E.11.5.9 | $T_1$ | 1 |
|  | E.11.5.11 | $T_1$ | 1 |
|  | E.12.5.4 | $T_1$ | 1 |
|  | E.12.5.10 | $T_1$ | 1 |
|  | E.12.5.18 | $T_1$ | 1 |
| Control wild-type | WT | — | 0 |
| Control non-transgenic | NT | — | 0 |

TABLE 3

Absence of the penalty in cotton fiber properties from five transgenic events compared to the wild-type (WT) and non-transgenic (NT) plants growth in greenhouse conditions provide by High Volume Instrument (HVI ™; United States Department of Agriculture, Cotton Division, USA). Micronaire index (MIC; μg/inch), elongation at fiber fracture (ELG; %), cotton yellowing degree/color grade (+B), impurity content (CNT), short-fiber index (SFI; %), count strength product (CSP), spinning consistency index (SCI), fiability index (CSP/SCI), maturity of cotton fiber (MAT; %), reflectance degree (RD) or brightness, uniformity index length (UI; %), strength (STR; gf/tex), length (LEN), mean upper-half length (UHML; inch), length (LEN/UHML; mm), percentage of the area occupied by the sum of impure particles (AF), leaf grade (impurity; LG), color grade (CG), and stickiness (ST). Values in parentheses represent the confidence interval from 2 biological replicates (cotton bolls harvested from 8 to 10 plants represent one biological replicate). Significant differences from WT and NT plants were checked with Tukey's test at 5%.

| Event | MIC | ELG (%) | +B | CNT | SFI (%) | CSP | SCI | CSP/SCI | MAT (%) |
|---|---|---|---|---|---|---|---|---|---|
| WT | 4.9 (0.1) | 6.4 (0.5) | 8.1 (0.0) | 6.5 (0.7) | 6.5 (1.2) | 2359 (84.5) | 152 (16.6) | 15.6 (1.1) | 87.5 (0.7) |
| NT | 3.9 (0.5) | 7.2 (0.0) | 8.1 (0.4) | 4.5 (2.1) | 4.8 (0.1) | 2612 (62.4) | 191 (9.7) | 13.7 (0.4) | 85.0 (1.4) |
| E7.4 | 4.4 (0.2) | 6.8 (0.1) | 8.0 (0.0) | 3.0 (1.4) | 5.2 (0.5) | 2487 (16.6) | 160 (4.9) | 15.5 (0.4) | 86.5 (0.7) |
| E12.5 | 4.8 (0.1) | 6.8 (0.2) | 8.2 (0.1) | 6.5 (0.7) | 5.0 (0.3) | 2504 (100.5) | 180 (15.2) | 13.9 (0.6) | 87.0 (0.0) |
| E11.5 | 5.0 (0.2) | 6.2 (0.2) | 8.6 (0.3) | 5.5 (0.7) | 6.6 (0.6) | 2374 (3.5) | 163 (2.1) | 14.5 (0.2) | 88.5 (0.7) |
| E7.3 | 4.7 (0.0) | 6.3 (0.2) | 8.3 (0.0) | 6.0 (1.4) | 6.2 (0.8) | 2362 (83.2) | 156 (15.9) | 15.1 (1.0) | 87.0 (0.0) |
| E2.4.2 | 4.1 (0.2) | 6.6 (0.0) | 7.7 (0.3) | 6.5 (2.1) | 5.9 (0.7) | 2515 (59.6) | 178 (6.9) | 14.1 (0.2) | 86.0 (0.0) |
| Tukey 5% | ns | ns | ns | ns | ns | ns | ns | ns | ns |

| Event | RD | UI (%) | STR | LEN | UHML | LEN/UHML | AF | LF | CG | ST |
|---|---|---|---|---|---|---|---|---|---|---|
| WT | 81.6 (0.6) | 83.2 (2.6) | 35.1 (0.7) | 31.3 (0.7) | 1.2 (0.0) | 25.4 | 0.1 (0.0) | 1.0 (0.0) | 21.2 | 4.5 (3.5) |
| NT | 80.8 (0.6) | 87.1 (1.0) | 37.4 (0.1) | 33.9 (0.1) | 1.3 (0.0) | 25.4 | 0.1 (0.0) | 1.0 (0.0) | 21.2 | 2.5 (0.7) |
| E7.4 | 82.2 (0.3) | 84.6 (0.6) | 32.8 (2.5) | 33.3 (0.5) | 1.3 (0.0) | 25.3 | 0.1 (0.0) | 1.0 (0.0) | 21.2 | 2.5 (2.1) |
| E12.5 | 82.4 (0.5) | 87.1 (1.9) | 36.7 (0.8) | 32.7 (1.4) | 1.3 (0.1) | 25.4 | 0.1 (0.0) | 1.0 (0.0) | 21.2 | 2.5 (0.7) |
| E11.5 | 80.5 (0.0) | 84.3 (0.8) | 37.1 (0.6) | 31.7 (1.3) | 1.3 (0.1) | 25.4 | 0.1 (0.0) | 1.0 (0.0) | 21.2 | 2.0 (0.0) |
| E7.3 | 80.4 (0.1) | 84.9 (0.3) | 33.8 (3.9) | 31.1 (1.2) | 1.2 (0.0) | 25.4 | 0.1 (0.0) | 1.0 (0.0) | 21.2 | 2.0 (0.0) |
| E2.4.2 | 81.8 (0.6) | 85.3 (0.9) | 37.5 (0.3) | 32.2 (0.6) | 1.3 (0.0) | 25.4 | 0.7 (0.6) | 2.5 (1.1) | 21.2 | 2.3 (0.0) |
| Tukey 5% | Ns | ns | ns | ns | ns | ns | ns | ns | ns | ns |

TABLE 4

Productivity measurements of independent soybean events, which using the dsRNA strategy to downregulation of the GmAIP10 genes, compared with nontransgenic (NT) plants. All events produced more seed weigth than the control non transformed ones. Most GM lines produced more seed pods and total number of seeds.

| Event number | Plant height | Leaf length | Leaf width | No pods | No seeds | Total weight of total seeds (g) | Weight of 100/ seeds (g) |
|---|---|---|---|---|---|---|---|
| Non-transformed lines ||||||||
| NT2 | 66.0 | 10.0 | 6.5 | 25 | 51 | 4.43 | 8.68627451 |
| NT3 | 64.0 | 11.5 | 7.5 | 28 | 65 | 4.53 | 6.969230769 |
| NT1 | 96.0 | 9.0 | 5.5 | 34 | 81 | 5.32 | 6.567901235 |
| Events with better performance ||||||||
| S18.2 | 75.0 | 12.0 | 7.5 | 44 | 94 | 12.25 | 13.03191489 |
| S19.8 | 88.5 | 12.5 | 7.5 | 44 | 87 | 10.97 | 12.6091954 |
| S19.3 | 105.5 | 12.5 | 7.0 | 41 | 90 | 10.78 | 11.97777778 |
| S18.7 | 65.0 | 12.0 | 8.0 | 38 | 94 | 10.69 | 11.37234043 |
| S18.17 | 70.5 | 12.5 | 8.0 | 34 | 81 | 10.49 | 12.95061728 |
| S18.19 | 115.0 | 12.0 | 7.5 | 37 | 88 | 10.31 | 11.71590909 |
| S21.5 | 94.5 | 14.5 | 9.0 | 39 | 77 | 9.24 | 12 |
| S18.11 | 68.5 | 11.5 | 7.0 | 36 | 87 | 8.93 | 10.26436782 |
| S18.4 | 81.0 | 10.5 | 6.0 | 43 | 91 | 8.45 | 9.285714286 |
| S21.14 | 114.0 | 13.5 | 8.5 | 31 | 73 | 8.38 | 11.47945205 |
| S19.6 | 69.0 | 11.5 | 7.0 | 38 | 84 | 8.38 | 9.976190476 |
| S20.4 | 68.0 | 12.5 | 7.2 | 34 | 78 | 8.32 | 10.66666667 |
| S20.1 | 93.0 | 12.5 | 7.5 | 35 | 77 | 7.81 | 10.14285714 |
| S18.15 | 71.5 | 10.5 | 5.5 | 40 | 83 | 7.75 | 9.337349398 |
| S19.11 | 75.5 | 15.5 | 8.5 | 36 | 88 | 7.69 | 8.738636364 |
| S21.11 | 71.0 | 13.0 | 7.5 | 30 | 62 | 7.48 | 12.06451613 |
| S20.8 | 81.5 | 11.5 | 7.0 | 29 | 59 | 7.4 | 12.54237288 |

Materials and Methods for Cotton Transgenic Constructs

Design of binary vector for the overexpression of the dsRNA and amiRNA to target and downregulate the cotton GhAIP10 genes is shown in FIG. 5, Panels A and B. The DNA sequences from cotton GhAIP10 genes used in the long dsRNA cloned into the binary vector is depicted in SEQ ID NO: 16 (forward sequence used in the dsRNA) and SEQ ID NO: 17 (reverse sequence used in the dsRNA). Sequences of cotton GhAIP10 genes (Gohir.A11G075200.1 (SEQ ID NO: 19), Gohir.A11G075200.2 (SEQ ID NO: 20), Gohir.D11G079900.1 (SEQ ID NO: 21), Gohir.D11G079900.2 (SEQ ID NO: 22), and Gohir.D11G079900.3, (SEQ ID NO: 23)) targeted in this invention are depicted in the sequence listing. Cotton sequences were proteins retrieved from the *Gossypium hirsutum* v1.1 (Upland cotton) genome dataset (Zhang T et al. (2015) *Nat. Biotechnol.* 33(5):531) or from the Phytozome v.12 database (Goodstein D M et al (2012) *Nucleic Acids Research* 40, D1178-D1186).

Materials and Methods for Soybean Transgenic Constructs

Design of binary vector for the overexpression of the dsRNA to target the GmAIP10 genes is depicted in FIG. 9A. Design of binary vector for the overexpression of the artificial miRNA (amiRNA) to target de GmAIP10 genes is depicted in FIG. 9B. The amiRNA sequence is depicted in SEQ ID NO: 29. The DNA sequences from soybean GmAIP10 genes used in the long dsRNA cloned into the binary vector are depicted in SEQ ID NO: 24 (Forward sequence used to generate the dsRNA) and SEQ ID NO: 25 (reverse sequence used to generate the dsRNA). Soybean AIP10 genes targeted in this invention are depicted in SEQ ID NOS: 26, 27 and 28. Soybean sequences were proteins retrieved from the *Glycine max* Wm82.a2.v1 (BioProject: PRJNA19861) genome dataset (Schmutz J et al (2010) *Nature* 463, 178-183) from the Phytozome v.12 database (Goodstein D M et al (2012) *Nucleic Acids Research* 40, D1178-D1186).

REFERENCES (The Contents of Each of which are Incorporated Herein by this Reference):

Aladjem M. I. Replication in context: dynamic regulation of DNA replication patterns in metazoans. *Nature Reviews Genetics*, v. 8, n. 8, pp. 588-600, 2007.

Berckmans B. and L. De Veylder. Transcriptional control of the cell cycle. *Current opinion in plant biology*, v. 12, n. 5, pp. 599-605, 2009.

Blow J. J. and A. Dutta. Preventing re-replication of chromosomal DNA. *Nat. Rev. Mol. Cell. Biol.*, v.6, n.6, pp. 476-86, 2005.

FAO-FOOD AND AGRICULTURE ORGANIZATION OF THE UNITED NATIONS. The State of Food Insecurity in the World Economic crises—impacts and lessons learned. [s.l: s.n.], 2012.

De Veylder L., T. Beeckman, and D. Inze. The ins and outs of the plant cell cycle. *Nature Reviews Molecular Cell Biology*, v. 8, n. 8, pp. 655-665, 2007.

Machida Y. J., J. L. Hamlin, and A. Dutta. Right place, right time, and only once: replication initiation in metazoans. *Cell.* 123:13-24, 2005.

Masuda H. P., L. M. Cabral, L. De Veylder, M. Tanurdzic, J. De Almeida-Engler, D. Geelen, D. Inze, P. C. G. Ferreira, R. A. Martienssen, and A. S. Hemerly. ABAP1 is a novel plant Armadillo BTB protein involved in DNA replication and transcription. *The EMBO journal*, v. 27, n. 20, pp. 2746-56, 22 out. 2008.

Morison J. I. L., N. R. Baker, P. M. Mullineaux, and W. J. Davies. Improving water use in crop production. *Philosophical transactions of the Royal Society of London. Series B, Biological sciences*, v. 363, n. 1491, pp. 639-58, 12 fev. 2008.

Parry M. A. J. and M. J. Hawkesford. An integrated approach to crop genetic improvement. *Journal of integrative plant biology*, v. 54, n. 4, pp. 250-9, abr. 2012.

Ramirez-Parra E., B. Desvoyes, and C. Gutierrez. Balance between cell division and differentiation during plant development. *The International Journal of Developmental Biology*, v. 49, 2005.

Sun J. and D. Kong. DNA replication origins, ORC/DNA interaction, and assembly of pre-replication complex in eukaryotes. *Acta. Biochim. Biophys. Sin.*, v. 42, n. 7, pp. 433-439, 2010.

What is claimed is:

1. A cultivated crop plant having a reduced level of functional wild-type AIP10 protein in comparison to a wild-type cultivated crop plant, wherein the cultivated crop plant comprises: a silencing RNA construct directed to AIP10 mRNA, an artificial microRNA directed to AIP10 mRNA, or a genome editing construct directed to an AIP10 gene, wherein the AIP10 protein comprises peptides having at least 90% sequence identity with SEQ ID NO: 39 and SEQ ID NO: 40 and wherein the reduced level of functional wild type AIP10 protein is reduced by expression of the silencing RNA construct, the artificial microRNA or genome editing construct.

2. The cultivated crop plant of claim 1, wherein the cultivated crop plant is selected from the group consisting of rice, wheat, barley, corn, soybean, cotton, sugarcane, sorghum, millet, rye, oats, cocoa, beans, grape, tomato, cassava, castor bean, poplar, eucalyptus, papaya, and oilseed.

3. A seed or plant cell having a reduced level of functional wild-type AIP10 protein derived from the cultivated crop plant of claim 1, wherein the reduced level of functional wild type AIP10 protein has been reduced by the silencing RNA construct, the artificial microRNA or the genome editing construct.

4. A seed or plant cell having a reduced level of functional wild-type AIP10 protein derived from the cultivated crop plant of claim 2, wherein the reduced level of functional wild type AIP10 protein is reduced by the silencing RNA construct, the artificial microRNA or genome editing construct.

5. A recombinant vector comprising:
a silencing RNA construct directed to AIP10 mRNA,
an artificial microRNA directed to AIP10 mRNA, or
a gene editing construct directed to an AIP10 gene,
wherein the AIP10 mRNA or AIP10 gene encodes an AIP10 protein comprising peptides having at least 90% sequence identity with SEQ ID NO: 39 and SEQ ID NO: 40.

6. A plant, plant cell, or plant seed comprising the recombinant vector of claim 5.

7. A method for increasing biomass, yield, and/or tolerance to drought in a cultivated crop plant, the method comprising:

reducing expression of a polynucleotide in the cultivated crop plant that encodes an AIP10 polypeptide comprising SEQ ID NO: 39 and SEQ ID NO: 40, or a polynucleotide that encodes an AIP10 polypeptide comprising peptides having at least 90% sequence identity with SEQ ID NO: 39 and SEQ ID NO: 40, so as to increase biomass, yield, and/or tolerance to drought in the cultivated crop plant, wherein the reduced expression of the polynucleotide that encodes the AIP10 polypeptide is obtained by introducing into the cultivated crop plant:
a silencing RNA construct directed to AIP10 mRNA,
an artificial microRNA directed to AIP10 mRNA, or
a genome editing construct directed to an AIP10 gene.

8. The method according to claim 7, wherein the AIP10 polypeptide comprises SEQ ID NO: 41.

9. The method according to claim 7, wherein the AIP10 polypeptide comprises SEQ ID NO: 42.

10. The method according to claim 7, wherein the polynucleotide encodes the polypeptide of SEQ ID NO: 30.

11. The method according to claim 7, wherein the polynucleotide encodes the polypeptide of SEQ ID NO: 31.

12. The method according to claim 7, wherein the polynucleotide encodes the polypeptide of SEQ ID NO: 32.

13. The method according to claim 7, wherein the polynucleotide encodes the polypeptide of SEQ ID NO: 33.

14. The method according to claim 7, wherein the polynucleotide encodes the polypeptide of SEQ ID NO: 34.

15. The method according to claim 7, wherein the polynucleotide encodes the polypeptide of SEQ ID NO: 35.

16. The method according to claim 7, wherein the polynucleotide encodes the polypeptide of SEQ ID NO: 36.

17. The method according to claim 7, wherein the polynucleotide encodes the polypeptide of SEQ ID NO: 37.

18. The method according to claim 7, wherein the polynucleotide encodes the polypeptide of SEQ ID NO: 38.

19. The cultivated crop plant of claim 1, wherein the AIP10 protein comprises SEQ ID NO: 39 and SEQ ID NO: 40.

20. The recombinant vector of claim 5, wherein the AIP10 mRNA or AIP10 gene encodes an AIP10 protein comprising SEQ ID NO: 39 and SEQ ID NO: 40.

* * * * *

SEQUENCE LISTING

```
<160> NUMBER OF SEQ ID NOS: 42

<210> SEQ ID NO 1
<211> LENGTH: 636
<212> TYPE: DNA
<213> ORGANISM: Zea mays

<400> SEQUENCE: 1
atggaggagc ccgttccggc tgatccccccc aggattttct ggaagtcaag gagttcaggt      60
tcagccaatg gccggagcct gcaacaagag cctgacaaag acgctaccga ggaaactaac     120
gagcaggctc aagaggaacc catgaagacc gacgacgcaa cggacacagc agcagcagca     180
gcagctacag ctgagccgta cccgaaagct aacctatccg agaagcggaa ggctctcttc     240
gagcctctcg agccgatcaa cggcaagcgc ggcgctgctg agacgctgct cccaccgccg     300
gactttgagc ccgcgtcgta ccccaagggg tggctggtgg gcaagaaacg caagctcgtc     360
aacgtagacg tcgtggagag catgcggagg attgcgatcc aggaaatgaa cagaaaggac     420
cgtgagatca atgggctgaa cgagcagcta gaggaagact cccgcgtgct ggagcttctg     480
cagaagcagc tggctgacga gcgcaggaag cggacagaga tcgagaagga gaactccatg     540
ctccatgagc aggtcaccat gctgatgaac atgctcgacg agaacgaggg tttcgacgag     600
gacggagagg ccccgccgcc cgattccttc gattaa                               636

<210> SEQ ID NO 2
<211> LENGTH: 20
<212> TYPE: DNA
<213> ORGANISM: Artificial Sequence
<220> FEATURE:
<223> OTHER INFORMATION: artificial gRNA (gRNA1) designed to target exon
      1 of the maize AIP10 gene

<400> SEQUENCE: 2 cctggggga tcagccggaa                                                    20

<210> SEQ ID NO 3
<211> LENGTH: 20
<212> TYPE: DNA
<213> ORGANISM: Artificial Sequence
<220> FEATURE:
<223> OTHER INFORMATION: artificial gRNA (gRNA2) designed to target exon
      2 of the maize AIP10 gene

<400> SEQUENCE: 3
taacctatcc gagaagcgga                                                   20

<210> SEQ ID NO 4
<211> LENGTH: 72
<212> TYPE: DNA
<213> ORGANISM: Artificial Sequence
<220> FEATURE:
<223> OTHER INFORMATION: primer

<400> SEQUENCE: 4
```

```
atatatggtc tctggcgacc tgggggatc agccggaagt tttagagcta gaaatagcaa      60
gttaaaataa gg                                                         72

<210> SEQ ID NO 5
<211> LENGTH: 52
<212> TYPE: DNA
<213> ORGANISM: Artificial Sequence
<220> FEATURE:
<223> OTHER INFORMATION: primer

<400> SEQUENCE: 5
ttattggtct ctaaactccg cttctcggat aggttatgct tcttggtgcc gc              52

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggcccagagc cacaagataa                                                  20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gcttgtggac cgaaacgaag                                                  20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
catcctcgtc actcgctaac                                                  20

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
acatgaacgc gtactcttta ttatc                                            25

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cgagatggcg aaggttgacg                                                  20

<210> SEQ ID NO 11
<211> LENGTH: 20
```

```
<212> TYPE: DNA
<213> ORGANISM: Artificial Sequence
<220> FEATURE:
<223> OTHER INFORMATION: primer

<400> SEQUENCE: 11
aatgtccgct gcttcctcag                                                 20

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
ctttgagccc gcgtcgta                                                   18

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
cgtcagccag ctgcttct                                                   18

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
accttaccag cccttgacat atg                                             23

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
gacttgacca aacatctcac gac                                             23

<210> SEQ ID NO 16
<211> LENGTH: 300
<212> TYPE: DNA
<213> ORGANISM: Gossypium hirsutum

<400> SEQUENCE: 16
gcagagtctt tgcttccccc accagacttc gatgctgcga gctatccaaa gggctggctg     60
attggaaaga agaggaagct ggtaaatgtt gacgttgttg agagcatgcg aaggattgca    120
gtccaggaaa tgaatagaaa ggacagggaa attgatgggt tgaatgagca gttggaagaa    180
gatgcgaggt gcttagaaca tctgcaactt cagcttttac aagagaaaag taaaagatca    240
gaggtggaga gagaaaacgc aatgcttcaa gaacaggtat ccatgctgat gaatatgttg    300

<210> SEQ ID NO 17
<211> LENGTH: 300
<212> TYPE: DNA
```

<213> ORGANISM: Gossypium hirsutum

<400> SEQUENCE: 17

| caacatattc atcagcatgg atacctgttc ttgaagcatt gcgttttctc tctccacctc | 60 |
| tgatctttta cttttctctt gtaaaagctg aagttgcaga tgttctaagc acctcgcatc | 120 |
| ttcttccaac tgctcattca acccatcaat ttccctgtcc tttctattca tttcctggac | 180 |
| tgcaatcctt cgcatgctct caacaacgtc aacatttacc agcttcctct tctttccaat | 240 |
| cagccagccc tttggatagc tcgcagcatc gaagtctggt gggggaagca aagactctgc | 300 |

<210> SEQ ID NO 18
<211> LENGTH: 21
<212> TYPE: DNA
<213> ORGANISM: Gossypium hirsutum

<400> SEQUENCE: 18

| gaggtgctta gaacatctgc a | 21 |

<210> SEQ ID NO 19
<211> LENGTH: 669
<212> TYPE: DNA
<213> ORGANISM: Gossypium hirsutum

<400> SEQUENCE: 19

| atggagaaag aagagaagag gaagaagatg gaggttgatt cagttccagc agcagctttg | 60 |
| gaagggtttt caccagtctc tacaactagg attttctgga attccaggaa aagatctgaa | 120 |
| tgttttaact tctctccgac agctagcggg aggaatttag acaaggtaac agaagagact | 180 |
| gctaatgtga cacccaccaa acaggaagaa caaactcttg atcaagacaa tacaccagat | 240 |
| tccgctacct cgtctgaact ttccgagcgt cggaaggctc tctttgagcc actggaacct | 300 |
| attaaaaaca tcaatggccg gcaaccgtca gcagagtctt tgcttccccc accagacttc | 360 |
| gatgctgcga gctatccaaa gggctggcta atcggaaaga gaggaagct ggtaaatgtt | 420 |
| gacgttgttg agagcatgcg aaggattgca gtccaggaaa tgaatagaaa ggacagggaa | 480 |
| attgatgggt tgaatgagca gttggaagaa gatgcgaggt gcttagaaca tctgcaactt | 540 |
| cagcttttac aagagaaaag taaagatca gaggtggaga gagaaaacgc aatgcttcaa | 600 |
| gaacaggtat ccatgctgat gaatatgttg caggaaggtg aggaaggtcc agatgatcat | 660 |
| gaaccttga | 669 |

<210> SEQ ID NO 20
<211> LENGTH: 645
<212> TYPE: DNA
<213> ORGANISM: Gossypium hirsutum

<400> SEQUENCE: 20

| atggagaaag aagagaagag gaagaagatg gaggttgatt cagttccagc agcagctttg | 60 |
| gaagggtttt caccagtctc tacaactagg attttctgga attccaggaa aagatctgct | 120 |
| agcgggagga atttagacaa ggtaacagaa gagactgcta atgtgacacc caccaaacag | 180 |
| gaagaacaaa ctcttgatca agacaataca ccagattccg ctacctcgtc tgaactttcc | 240 |
| gagcgtcgga aggctctctt tgagccactg gaacctatta aaaacatcaa tggccggcaa | 300 |
| ccgtcagcag agtctttgct tccccaccacca gacttcgatg ctgcgagcta tccaagggc | 360 |
| tggctaatcg gaagaagag gaagctggta atgttgacg ttgttgagag catgcgaagg | 420 |
| attgcagtcc aggaaatgaa tagaaaggac agggaaattg atgggttgaa tgagcagttg | 480 |

```
gaagaagatg cgaggtgctt agaacatctg caacttcagc ttttacaaga gaaaagtaaa    540
agatcagagg tggagagaga aaacgcaatg cttcaagaac aggtatccat gctgatgaat    600
atgttgcagg aaggtgagga aggtccagat gatcatgaac cttga                   645
```

<210> SEQ ID NO 21
<211> LENGTH: 645
<212> TYPE: DNA
<213> ORGANISM: Gossypium hirsutum

<400> SEQUENCE: 21

```
atggagaaag aagagaagaa gaagaagatg gaggtagatt cagctccagc agcagctttg     60
gaagggtttt caccagtctc tacaactagg attttctgga attccaggaa aagatctgct    120 agcggggagga atttagacaa ggtaacagaa gagactgcta atgtgacacc caccaaacag    180
gaagaacaaa ctcttgatca agacaataca ccggattccg ctacctcttc tgaactttcc    240
gagcgtcgga aggctctctt tgaaccactg gaacctatta aaaacatcaa tggccggcga    300
ccatcagctg agtctttgct tcccccacca gacttcgatg ctgcgagcta tccaaagggc    360
tggctgattg gaaagaagag gaagctggta atgttgacg ttgttgagag catgcggagg     420
attgcagtcc aggaaatgaa tagaaaggac agggaaattg atgggttgaa tgagcagttg    480
gaagaagatg cgaggtgctt agaacatctg caacttcagc ttttacaaga gaaaagtaaa    540
agatcagagg tggagagaga aaacgcaatg cttcaagaac aggtatccat gctgatgaat    600
atgttgcagg aaggtgagga aggtccagat gatcatgaac cttga                   645
```

<210> SEQ ID NO 22
<211> LENGTH: 588
<212> TYPE: DNA
<213> ORGANISM: Gossypium hirsutum

<400> SEQUENCE: 22

```
atggagaaag aagagaagaa gaagaagatg gaggtagatt cagctccagc agcagctttg     60
gaagggtttt caccagtctc tacaactagg attttctgga attccaggaa aagatctgct    120 agcggggagga atttagacaa ggtaacagaa gagactgcta atgtgacacc caccaaacag    180
gaagaacaaa ctcttgatca agacaataca ccggattccg ctacctcttc tgaactttcc    240
gagcgtcgga aggctctctt tgaaccactg gaacctatta aaaacatcaa tggccggcga    300
ccatcagctg agtctttgct tcccccacca gacttcgatg ctgcgagcta tccaaagggc    360
tggctgattg gaaagaagag gaagctggta atgttgacg ttgttgagag catgcggagg     420
attgcagtcc aggaaatgaa tagaaaggac agggaaattg atgggttgaa tgagcagttg    480
gaagaagatg cgaggtgctt agaacatctg caacttcagc ttttacaaga gaaaagtaaa    540
agatcagagg tggagagaga aaacgcaatg cttcaagaac agagttag                588
```

<210> SEQ ID NO 23
<211> LENGTH: 486
<212> TYPE: DNA
<213> ORGANISM: Gossypium hirsutum

<400> SEQUENCE: 23

```
atggagaaag aagagaagaa gaagaagatg gaggtagatt cagctccagc agcagctttg     60
gaagggtttt caccagtctc tacaactagg attttctgga attccaggaa aagatctgct    120 agcggggagga atttagacaa ggtaacagaa gagactgcta atgtgacacc caccaaacag    180
```

```
gaagaacaaa ctcttgatca agacaataca ccggattccg ctacctcttc tgaactttcc        240
gagcgtcgga aggctctctt tgaaccactg gaacctatta aaaacatcaa tggccggcga        300
ccatcagctg agtctttgct tcccccacca gacttcgatg ctgcgagcta ccaaagggc         360 tggctgattg aaagaagag gaagctggta aatgttgacg ttgttgagag catgcggagg         420
attgcagtcc aggaaatgaa tagaaaggtc tcatgtcata tacttaacct cctctcaaaa        480
cactag                                                                    486
```

```
<210> SEQ ID NO 24
<211> LENGTH: 300
<212> TYPE: DNA
<213> ORGANISM: Glycine max

<400> SEQUENCE: 24
gctgagtctt tacttcctcc ccctgacttt gagtttgcaa actatccaaa gggctggttg         60
attggcaaga agagaaagct tgttaatgtc gatgttgttg aaagcatgcg aaggattgcc        120
atccaagaaa tgaacagaaa ggacaggaa attgatgggc taaatgaaca gttggaggag        180
gattcacggt gtttagagca cttgcaactc cagattgtgg atgaaaaaag caaacgtgct        240
agagtggaaa gagaaaatgc aatgcttcaa gaacaagtga acatgcttat gaacatgtta        300
```

```
<210> SEQ ID NO 25
<211> LENGTH: 300
<212> TYPE: DNA
<213> ORGANISM: Glycine max

<400> SEQUENCE: 25
taacatgttc ataagcatgt tcacttgttc ttgaagcatt gcattttctc tttccactct         60
agcacgtttg ctttttttcat ccacaatctg gagttgcaag tgctctaaac accgtgaatc        120
ctcctccaac tgttcattta gcccatcaat ttccctgtcc tttctgttca tttcttggat        180
ggcaatcctt cgcatgcttt caacaacatc gacattaaca agctttctct tcttgccaat        240
caaccagccc tttggatagt ttgcaaactc aaagtcaggg ggaggaagta aagactcagc        300
```

```
<210> SEQ ID NO 26
<211> LENGTH: 645
<212> TYPE: DNA
<213> ORGANISM: Glycine max

<400> SEQUENCE: 26
atggaaacac gtgctggaag tgatatgaag atggccatag atgatgcttt gaacgccttc         60
tctcctgttt ccaccccag gattttctgg aaatcacgaa ggagatcagc tagcgggagg        120
aatttagagg tatcagaaga tactgctaat aaaccaccca gcaagcagga agatactcct        180
cctcctcctc ctccaccttc tagtgaggag gtgcagaaca cgactccgat ttctgagcgc        240
cgaaaggcct tgtttgaacc gttagaaccc ataatgaata ttaatggccg acgacccttg        300
gctgagtctt tacttcctcc ccctgacttt gagtctgcaa actatccaaa gggctggttg        360
attggcaaga agagaaagct tgttaatgtc gatgttgttg aaagcatgcg aaggattgcc        420
atccaagaaa tgaacagaaa ggacaggaa attgatgggc taaatgaaca gctggaggag        480
gattcacggt gtctagagca cttgcaactc agcttgtgg atgaaaaaag caaacgtgct        540
agagtggaaa gagaaaatgc aatgcttcaa gaacaagtga acatgcttat gaacatgtta        600
caagaagcag aacaaatggg agatgaaggc cctgatgaac cttaa                        645
```

<210> SEQ ID NO 27
<211> LENGTH: 564
<212> TYPE: DNA
<213> ORGANISM: Glycine max

<400> SEQUENCE: 27

| atggaaacac gtgctggaag tgatatgaag atggccatag atgatgcttt gaacgccttc | 60 |
| tctcctgttt ccaccccag gattttctgg aaatcacgaa ggagatcagc tagcgggagg | 120 |
| aatttagagg tatcagaaga tactgctaat aaaccaccca gcaagcagga agatactcct | 180 |
| cctcctcctc ctccaccttc tagtgaggag gtgcagaaca cgactccgat ttctgagcgc | 240 |
| cgaaaggcct tgtttgaacc gttagaaccc ataatgaata ttaatggccg acgacccttg | 300 |
| gctgagtctt acttcctcc ccctgacttt gagtctgcaa actatccaaa gggctggttg | 360 |
| attggcaaga gagaaagct tgttaatgtc gatgttgttg aaagcatgcg aaggattgcc | 420 |
| atccaagaaa tgaacagaaa ggttccaagt tcctcaaca ccttcacttc caaacaaaga | 480 |
| cacaattata ctgagccacc tgctcatttt gttgttgttg ttgttgtaat tgttgcttgc | 540 |
| aggacaggga aattgatggg ctaa | 564 |

<210> SEQ ID NO 28
<211> LENGTH: 633
<212> TYPE: DNA
<213> ORGANISM: Glycine max

<400> SEQUENCE: 28

| atggaaacac gtgctagtgg tgatatgaag atggccatag atgatgcttt gaatggcttc | 60 |
| tctcctgtct ccaccccag gattttctgg aaatcacgaa ggagatcagc tagcgggagg | 120 |
| aatttagagg tatcagaaga tactgctaat aaaccaccca gcaagcagga agatactcct | 180 |
| ccaccttcta gtgaggaggt gcagaacacg actccgattt ctgagcgccg aaaggctctg | 240 |
| tttgaacctt tagaacctat aatgaatatt aatggccgac gacctcggc cgagtcttta | 300 |
| cttcctcctc ctgactttga gtctgcaaac tatccgaagg gctggctgat tggcaagaag | 360 |
| agaaaactcg ttaatgtcga tgttgttgaa agcatgagaa ggattgccat ccaagaaatg | 420 |
| aacagaaagg acagggaaat tgatgggctg aatgaacagc tggaggagga ttcacggtgt | 480 |
| ctagagcact tgcaactcca gcttgtggat gaaaaaagca acgcgctcg agtggaaaga | 540 |
| gaaaatgcaa tgctgcaaga acaagtgaac atgcttatga acatgttgca agaagcagaa | 600 |
| caaatgggag atgaaggccc agatgaacct taa | 633 |

<210> SEQ ID NO 29
<211> LENGTH: 21
<212> TYPE: DNA
<213> ORGANISM: Glycine max

<400> SEQUENCE: 29

| gcgccgaaag gccttgtttg a | 21 |

<210> SEQ ID NO 30
<211> LENGTH: 211
<212> TYPE: PRT
<213> ORGANISM: Zea mays

<400> SEQUENCE: 30

Met Glu Glu Pro Val Pro Ala Asp Pro Pro Arg Ile Phe Trp Lys Ser
1               5                   10                  15

Arg Ser Ser Gly Ser Ala Asn Gly Arg Ser Leu Gln Gln Glu Pro Asp

```
            20                  25                  30
Lys Asp Ala Thr Glu Glu Thr Asn Glu Gln Ala Gln Glu Glu Pro Met
            35                  40                  45

Lys Thr Asp Asp Ala Thr Asp Thr Ala Ala Ala Ala Ala Thr Ala
 50                  55                  60

Glu Pro Tyr Pro Lys Ala Asn Leu Ser Glu Lys Arg Lys Ala Leu Phe
 65                  70                  75                  80

Glu Pro Leu Glu Pro Ile Asn Gly Lys Arg Gly Ala Ala Glu Thr Leu
                    85                  90                  95

Leu Pro Pro Pro Asp Phe Glu Pro Ala Ser Tyr Pro Lys Gly Trp Leu
                    100                 105                 110

Val Gly Lys Lys Arg Lys Leu Val Asn Val Asp Val Glu Ser Met
            115                 120                 125

Arg Arg Ile Ala Ile Gln Glu Met Asn Arg Lys Asp Arg Glu Ile Asn
 130                 135                 140

Gly Leu Asn Glu Gln Leu Glu Glu Asp Ser Arg Val Leu Glu Leu Leu
145                 150                 155                 160

Gln Lys Gln Leu Ala Asp Glu Arg Arg Lys Arg Thr Glu Ile Glu Lys
                    165                 170                 175

Glu Asn Ser Met Leu His Glu Gln Val Thr Met Leu Met Asn Met Leu
                    180                 185                 190

Asp Glu Asn Glu Gly Phe Asp Glu Asp Gly Glu Ala Pro Pro Pro Asp
                    195                 200                 205

Ser Phe Asp
    210

<210> SEQ ID NO 31
<211> LENGTH: 222
<212> TYPE: PRT
<213> ORGANISM: Gossypium hirsutum

<400> SEQUENCE: 31

Met Glu Lys Glu Glu Lys Arg Lys Lys Met Glu Val Asp Ser Val Pro
 1               5                  10                  15

Ala Ala Ala Leu Glu Gly Phe Ser Pro Val Ser Thr Thr Arg Ile Phe
                    20                  25                  30

Trp Asn Ser Arg Lys Arg Ser Glu Cys Phe Asn Phe Ser Pro Thr Ala
            35                  40                  45

Ser Gly Arg Asn Leu Asp Lys Val Thr Glu Glu Thr Ala Asn Val Thr
 50                  55                  60

Pro Thr Lys Gln Glu Glu Gln Thr Leu Asp Gln Asp Asn Thr Pro Asp
 65                  70                  75                  80

Ser Ala Thr Ser Ser Glu Leu Ser Glu Arg Arg Lys Ala Leu Phe Glu
                    85                  90                  95

Pro Leu Glu Pro Ile Lys Asn Ile Asn Gly Arg Gln Pro Ser Ala Glu
                    100                 105                 110

Ser Leu Leu Pro Pro Asp Phe Asp Ala Ala Ser Tyr Pro Lys Gly
            115                 120                 125

Trp Leu Ile Gly Lys Lys Arg Lys Leu Val Asn Val Asp Val Val Glu
            130                 135                 140

Ser Met Arg Arg Ile Ala Val Gln Glu Met Asn Arg Lys Asp Arg Glu
145                 150                 155                 160

Ile Asp Gly Leu Asn Glu Gln Leu Glu Glu Asp Ala Arg Cys Leu Glu
                    165                 170                 175
```

His Leu Gln Leu Gln Leu Leu Gln Glu Lys Ser Lys Arg Ser Glu Val
              180                 185                 190

Glu Arg Glu Asn Ala Met Leu Gln Glu Gln Val Ser Met Leu Met Asn
          195                 200                 205

Met Leu Gln Glu Gly Glu Gly Pro Asp Asp His Glu Pro
    210                 215                 220

<210> SEQ ID NO 32
<211> LENGTH: 214
<212> TYPE: PRT
<213> ORGANISM: Gossypium hirsutum

<400> SEQUENCE: 32

Met Glu Lys Glu Glu Lys Arg Lys Lys Met Glu Val Asp Ser Val Pro
1               5                   10                  15

Ala Ala Ala Leu Glu Gly Phe Ser Pro Val Ser Thr Thr Arg Ile Phe
            20                  25                  30

Trp Asn Ser Arg Lys Arg Ser Ala Ser Gly Arg Asn Leu Asp Lys Val
        35                  40                  45

Thr Glu Glu Thr Ala Asn Val Thr Pro Thr Lys Gln Glu Glu Gln Thr
    50                  55                  60

Leu Asp Gln Asp Asn Thr Pro Asp Ser Ala Thr Ser Ser Glu Leu Ser
65                  70                  75                  80

Glu Arg Arg Lys Ala Leu Phe Glu Pro Leu Glu Pro Ile Lys Asn Ile
                85                  90                  95

Asn Gly Arg Gln Pro Ser Ala Glu Ser Leu Leu Pro Pro Asp Phe
            100                 105                 110

Asp Ala Ala Ser Tyr Pro Lys Gly Trp Leu Ile Gly Lys Lys Arg Lys
            115                 120                 125

Leu Val Asn Val Asp Val Val Glu Ser Met Arg Arg Ile Ala Val Gln
        130                 135                 140

Glu Met Asn Arg Lys Asp Arg Glu Ile Asp Gly Leu Asn Glu Gln Leu
145                 150                 155                 160

Glu Glu Asp Ala Arg Cys Leu Glu His Leu Gln Leu Gln Leu Leu Gln
                165                 170                 175

Glu Lys Ser Lys Arg Ser Glu Val Glu Arg Glu Asn Ala Met Leu Gln
            180                 185                 190

Glu Gln Val Ser Met Leu Met Asn Met Leu Gln Glu Gly Glu Gly
        195                 200                 205

Pro Asp Asp His Glu Pro
    210

<210> SEQ ID NO 33
<211> LENGTH: 214
<212> TYPE: PRT
<213> ORGANISM: Gossypium hirsutum

<400> SEQUENCE: 33

Met Glu Lys Glu Glu Lys Lys Lys Met Glu Val Asp Ser Ala Pro
1               5                   10                  15

Ala Ala Ala Leu Glu Gly Phe Ser Pro Val Ser Thr Thr Arg Ile Phe
            20                  25                  30

Trp Asn Ser Arg Lys Arg Ser Ala Ser Gly Arg Asn Leu Asp Lys Val
        35                  40                  45

Thr Glu Glu Thr Ala Asn Val Thr Pro Thr Lys Gln Glu Glu Gln Thr
    50                  55                  60

```
Leu Asp Gln Asp Asn Thr Pro Asp Ser Ala Thr Ser Ser Glu Leu Ser
 65                  70                  75                  80

Glu Arg Arg Lys Ala Leu Phe Glu Pro Leu Glu Pro Ile Lys Asn Ile
                 85                  90                  95

Asn Gly Arg Arg Pro Ser Ala Glu Ser Leu Leu Pro Pro Asp Phe
             100                 105                 110

Asp Ala Ala Ser Tyr Pro Lys Gly Trp Leu Ile Gly Lys Lys Arg Lys
             115                 120                 125

Leu Val Asn Val Asp Val Val Glu Ser Met Arg Arg Ile Ala Val Gln
         130                 135                 140

Glu Met Asn Arg Lys Asp Arg Glu Ile Asp Gly Leu Asn Glu Gln Leu
145                 150                 155                 160

Glu Glu Asp Ala Arg Cys Leu Glu His Leu Gln Leu Gln Leu Leu Gln
                165                 170                 175

Glu Lys Ser Lys Arg Ser Glu Val Glu Arg Glu Asn Ala Met Leu Gln
                180                 185                 190

Glu Gln Val Ser Met Leu Met Asn Met Leu Gln Glu Gly Glu Gly
            195                 200                 205

Pro Asp Asp His Glu Pro
    210

<210> SEQ ID NO 34
<211> LENGTH: 195
<212> TYPE: PRT
<213> ORGANISM: Gossypium hirsutum

<400> SEQUENCE: 34

Met Glu Lys Glu Glu Lys Lys Lys Met Glu Val Asp Ser Ala Pro
1                5                  10                  15

Ala Ala Ala Leu Glu Gly Phe Ser Pro Val Ser Thr Thr Arg Ile Phe
             20                  25                  30

Trp Asn Ser Arg Lys Arg Ser Ala Ser Gly Arg Asn Leu Asp Lys Val
         35                  40                  45

Thr Glu Glu Thr Ala Asn Val Thr Pro Thr Lys Gln Glu Glu Gln Thr
 50                  55                  60

Leu Asp Gln Asp Asn Thr Pro Asp Ser Ala Thr Ser Ser Glu Leu Ser
 65                  70                  75                  80

Glu Arg Arg Lys Ala Leu Phe Glu Pro Leu Glu Pro Ile Lys Asn Ile
                 85                  90                  95

Asn Gly Arg Arg Pro Ser Ala Glu Ser Leu Leu Pro Pro Asp Phe
             100                 105                 110

Asp Ala Ala Ser Tyr Pro Lys Gly Trp Leu Ile Gly Lys Lys Arg Lys
             115                 120                 125

Leu Val Asn Val Asp Val Val Glu Ser Met Arg Arg Ile Ala Val Gln
         130                 135                 140

Glu Met Asn Arg Lys Asp Arg Glu Ile Asp Gly Leu Asn Glu Gln Leu
145                 150                 155                 160

Glu Glu Asp Ala Arg Cys Leu Glu His Leu Gln Leu Gln Leu Leu Gln
                165                 170                 175

Glu Lys Ser Lys Arg Ser Glu Val Glu Arg Glu Asn Ala Met Leu Gln
                180                 185                 190

Glu Gln Ser
        195

<210> SEQ ID NO 35
```

<211> LENGTH: 161
<212> TYPE: PRT
<213> ORGANISM: Gossypium hirsutum

<400> SEQUENCE: 35

Met Glu Lys Glu Glu Lys Lys Lys Met Glu Val Asp Ser Ala Pro
1               5                   10                  15

Ala Ala Ala Leu Glu Gly Phe Ser Pro Val Ser Thr Thr Arg Ile Phe
            20                  25                  30

Trp Asn Ser Arg Lys Arg Ser Ala Ser Gly Arg Asn Leu Asp Lys Val
                35                  40                  45

Thr Glu Glu Thr Ala Asn Val Thr Pro Thr Lys Gln Glu Glu Gln Thr
50                  55                  60

Leu Asp Gln Asp Asn Thr Pro Asp Ser Ala Thr Ser Ser Glu Leu Ser
65                  70                  75                  80

Glu Arg Arg Lys Ala Leu Phe Glu Pro Leu Glu Pro Ile Lys Asn Ile
                85                  90                  95

Asn Gly Arg Arg Pro Ser Ala Glu Ser Leu Leu Pro Pro Pro Asp Phe
            100                 105                 110

Asp Ala Ala Ser Tyr Pro Lys Gly Trp Leu Ile Gly Lys Lys Arg Lys
        115                 120                 125

Leu Val Asn Val Asp Val Val Glu Ser Met Arg Arg Ile Ala Val Gln
130                 135                 140

Glu Met Asn Arg Lys Val Ser Cys His Ile Leu Asn Leu Leu Ser Lys
145                 150                 155                 160

His

<210> SEQ ID NO 36
<211> LENGTH: 214
<212> TYPE: PRT
<213> ORGANISM: Glycine max

<400> SEQUENCE: 36

Met Glu Thr Arg Ala Gly Ser Asp Met Lys Met Ala Ile Asp Asp Ala
1               5                   10                  15

Leu Asn Ala Phe Ser Pro Val Ser Thr Pro Arg Ile Phe Trp Lys Ser
            20                  25                  30

Arg Arg Arg Ser Ala Ser Gly Arg Asn Leu Glu Val Ser Glu Asp Thr
        35                  40                  45

Ala Asn Lys Pro Pro Ser Lys Gln Glu Asp Thr Pro Pro Pro Pro
50                  55                  60

Pro Pro Ser Ser Glu Glu Val Gln Asn Thr Thr Pro Ile Ser Glu Arg
65                  70                  75                  80

Arg Lys Ala Leu Phe Glu Pro Leu Glu Pro Ile Met Asn Ile Asn Gly
                85                  90                  95

Arg Arg Pro Leu Ala Glu Ser Leu Leu Pro Pro Asp Phe Glu Ser
            100                 105                 110

Ala Asn Tyr Pro Lys Gly Trp Leu Ile Gly Lys Lys Arg Lys Leu Val
        115                 120                 125

Asn Val Asp Val Val Glu Ser Met Arg Arg Ile Ala Ile Gln Glu Met
130                 135                 140

Asn Arg Lys Asp Arg Glu Ile Asp Gly Leu Asn Glu Gln Leu Glu Glu
145                 150                 155                 160

Asp Ser Arg Cys Leu Glu His Leu Gln Leu Gln Leu Val Asp Glu Lys
            165                 170                 175

```
Ser Lys Arg Ala Arg Val Glu Arg Glu Asn Ala Met Leu Gln Glu Gln
            180                 185                 190

Val Asn Met Leu Met Asn Met Leu Gln Glu Ala Glu Gln Met Gly Asp
        195                 200                 205

Glu Gly Pro Asp Glu Pro
    210

<210> SEQ ID NO 37
<211> LENGTH: 187
<212> TYPE: PRT
<213> ORGANISM: Glycine max

<400> SEQUENCE: 37

Met Glu Thr Arg Ala Gly Ser Asp Met Lys Met Ala Ile Asp Asp Ala
1               5                   10                  15

Leu Asn Ala Phe Ser Pro Val Ser Thr Pro Arg Ile Phe Trp Lys Ser
            20                  25                  30

Arg Arg Arg Ser Ala Ser Gly Arg Asn Leu Glu Val Ser Glu Asp Thr
        35                  40                  45

Ala Asn Lys Pro Pro Ser Lys Gln Glu Asp Thr Pro Pro Pro Pro Pro
    50                  55                  60

Pro Pro Ser Ser Glu Glu Val Gln Asn Thr Thr Pro Ile Ser Glu Arg
65                  70                  75                  80

Arg Lys Ala Leu Phe Glu Pro Leu Glu Pro Ile Met Asn Ile Asn Gly
                85                  90                  95

Arg Arg Pro Leu Ala Glu Ser Leu Leu Pro Pro Asp Phe Glu Ser
            100                 105                 110

Ala Asn Tyr Pro Lys Gly Trp Leu Ile Gly Lys Lys Arg Lys Leu Val
        115                 120                 125

Asn Val Asp Val Val Glu Ser Met Arg Arg Ile Ala Ile Gln Glu Met
    130                 135                 140

Asn Arg Lys Val Pro Ser Phe Leu Asn Thr Phe Thr Ser Lys Gln Arg
145                 150                 155                 160

His Asn Tyr Thr Glu Pro Pro Ala His Phe Val Val Val Val Val Val
                165                 170                 175

Ile Val Ala Cys Arg Thr Gly Lys Leu Met Gly
            180                 185

<210> SEQ ID NO 38
<211> LENGTH: 210
<212> TYPE: PRT
<213> ORGANISM: Glycine max

<400> SEQUENCE: 38

Met Glu Thr Arg Ala Ser Gly Asp Met Lys Met Ala Ile Asp Asp Ala
1               5                   10                  15

Leu Asn Gly Phe Ser Pro Val Ser Thr Pro Arg Ile Phe Trp Lys Ser
            20                  25                  30

Arg Arg Arg Ser Ala Ser Gly Arg Asn Leu Glu Val Ser Glu Asp Thr
        35                  40                  45

Ala Asn Lys Pro Pro Ser Lys Gln Glu Asp Thr Pro Pro Ser Ser
    50                  55                  60

Glu Glu Val Gln Asn Thr Thr Pro Ile Ser Glu Arg Arg Lys Ala Leu
65                  70                  75                  80

Phe Glu Pro Leu Glu Pro Ile Met Asn Ile Asn Gly Arg Arg Pro Ser
                85                  90                  95
```

```
Ala Glu Ser Leu Leu Pro Pro Pro Asp Phe Glu Ser Ala Asn Tyr Pro
                100                 105                 110

Lys Gly Trp Leu Ile Gly Lys Lys Arg Lys Leu Val Asn Val Asp Val
        115                 120                 125

Val Glu Ser Met Arg Arg Ile Ala Ile Gln Glu Met Asn Arg Lys Asp
    130                 135                 140

Arg Glu Ile Asp Gly Leu Asn Glu Gln Leu Glu Asp Ser Arg Cys
145                 150                 155                 160

Leu Glu His Leu Gln Leu Gln Leu Val Asp Glu Lys Ser Lys Arg Ala
                165                 170                 175

Arg Val Glu Arg Glu Asn Ala Met Leu Gln Glu Gln Val Asn Met Leu
            180                 185                 190

Met Asn Met Leu Gln Glu Ala Glu Gln Met Gly Asp Glu Gly Pro Asp
        195                 200                 205

Glu Pro
    210

<210> SEQ ID NO 39
<211> LENGTH: 15
<212> TYPE: PRT
<213> ORGANISM: Zea mays

<400> SEQUENCE: 39

Leu Ser Glu Lys Arg Lys Ala Leu Phe Glu Pro Leu Glu Pro Ile
1               5                   10                  15

<210> SEQ ID NO 40
<211> LENGTH: 33
<212> TYPE: PRT
<213> ORGANISM: Zea mays

<400> SEQUENCE: 40

Tyr Pro Lys Gly Trp Leu Val Gly Lys Lys Arg Lys Leu Val Asn Val
1               5                   10                  15

Asp Val Val Glu Ser Met Arg Arg Ile Ala Ile Gln Glu Met Asn Arg
                20                  25                  30

Lys

<210> SEQ ID NO 41
<211> LENGTH: 15
<212> TYPE: PRT
<213> ORGANISM: Zea mays
<220> FEATURE:
<221> NAME/KEY: MISC_FEATURE
<222> LOCATION: (1)..(1)
<223> OTHER INFORMATION: X can be L or I
<220> FEATURE:
<221> NAME/KEY: MISC_FEATURE
<222> LOCATION: (4)..(4)
<223> OTHER INFORMATION: X can be K or R

<400> SEQUENCE: 41

Xaa Ser Glu Xaa Arg Lys Ala Leu Phe Glu Pro Leu Glu Pro Ile
1               5                   10                  15

<210> SEQ ID NO 42
<211> LENGTH: 33
<212> TYPE: PRT
<213> ORGANISM: Zea mays
<220> FEATURE:
<221> NAME/KEY: MISC_FEATURE
<222> LOCATION: (7)..(7)
<223> OTHER INFORMATION: X can be L or I
```

```
<220> FEATURE:
<221> NAME/KEY: MISC_FEATURE
<222> LOCATION: (27)..(27)
<223> OTHER INFORMATION: X can be I or V

<400> SEQUENCE: 42

Tyr Pro Lys Gly Trp Leu Xaa Gly Lys Lys Arg Lys Leu Val Asn Val
1               5                   10                  15

Asp Val Val Glu Ser Met Arg Arg Ile Ala Xaa Gln Glu Met Asn Arg
                20                  25                  30

Lys
```